United States Patent [19]
Johnson et al.

[11] Patent Number: 6,086,572
[45] Date of Patent: Jul. 11, 2000

[54] ELECTROTRANSPORT DEVICE AND METHOD OF SETTING OUTPUT

[75] Inventors: Susan A. Johnson, Vacaville, Calif.; Gary A. Lattin, Forest Lake; Larry A. McNichols, Coon Rapids, both of Minn.

[73] Assignee: ALZA Corporation, Mountain View, Calif.

[21] Appl. No.: 08/952,656

[22] PCT Filed: May 31, 1996

[86] PCT No.: PCT/US96/08242

§ 371 Date: Mar. 9, 1998

§ 102(e) Date: Mar. 9, 1998

[87] PCT Pub. No.: WO96/38198

PCT Pub. Date: Dec. 5, 1996

[51] Int. Cl.[7] ................................................ A61M 31/00
[52] U.S. Cl. .................... 604/503; 604/20; 604/30; 604/501
[58] Field of Search ................................ 604/20, 14, 30, 604/501, 503

[56] References Cited

U.S. PATENT DOCUMENTS

| | | | |
|---|---|---|---|
| 3,899,687 | 8/1975 | Jones | 250/568 |
| 3,922,529 | 11/1975 | Orloff | 235/61.11 H |
| 4,141,359 | 2/1979 | Jacobsen et al. | 128/172.1 |
| 4,474,570 | 10/1984 | Arirura et al. | 604/20 |
| 4,874,933 | 10/1989 | Sanner | 235/470 |
| 4,931,991 | 6/1990 | Cvjanovich | 365/52 |
| 5,006,108 | 4/1991 | LaPrade | 604/20 |
| 5,047,007 | 9/1991 | McNichols et al. | 604/20 |
| 5,125,894 | 6/1992 | Phipps et al. | 604/20 |
| 5,160,316 | 11/1992 | Henley | 604/20 |
| 5,224,927 | 7/1993 | Tapper | 604/20 |
| 5,224,928 | 7/1993 | Sibalis et al. | 604/20 |
| 5,246,418 | 9/1993 | Haynes et al. | 604/20 |
| 5,254,081 | 10/1993 | Maurer et al. | 604/20 |
| 5,430,278 | 7/1995 | Krieg et al. | 235/449 |
| 5,443,442 | 8/1995 | Phipps et al. | 604/20 |
| 5,451,763 | 9/1995 | Pickett et al. | 235/492 |
| 5,551,953 | 9/1996 | Lattin et al. | 604/20 |
| 5,591,124 | 1/1997 | Phipps | 604/20 |
| 5,622,530 | 4/1997 | Phipps | 604/20 |

FOREIGN PATENT DOCUMENTS

| | | | |
|---|---|---|---|
| 0060452 | 9/1982 | European Pat. Off. | A61N 1/24 |
| 0337642 | 10/1989 | European Pat. Off. | A61N 1/30 |
| 4028125 | 7/1991 | Germany | A61N 1/30 |
| 2239803A | 7/1991 | United Kingdom | A61N 1/30 |
| WO8607269 | 12/1986 | WIPO | A61N 1/30 |
| WO 94 28965 | 12/1994 | WIPO | A61M 37/00 |

OTHER PUBLICATIONS

Hayt, William H., "Engineering Electromagnetics", JC, 1981 McGraw Hill, pp 428–430.

"Websters Dictionary, 9th New Collegiate", See "bar code" and "scan" pp 130, 1047, 1048.

*Primary Examiner*—Wynn Wood Coggins
*Assistant Examiner*—Jennifer R. Sadula
*Attorney, Agent, or Firm*—Owen J. Bates; D. Byron Miller; Steven F. Stone

[57] ABSTRACT

A two-part electrotransport drug delivery device (20) is comprised of a controller (22) which has a plurality of different electronic outputs. The controller (22) is adapted to be mechanically and electrically coupled to a plurality of different drug-containing units (24). Each drug unit (24) includes a means (40, 42, Rx, Cx) for signaling the controller (22). The signal is read by the controller (22) and a predetermined electronic output is thereby selected and applied through the drug unit (24) in order to deliver the drug contained therein by electrotransport. The signal sent by the drug unit (24) to the controller (22) may be an optical signal (e.g., reflected light), a signal sent by an electromechanical connector, an electrical signal (e.g., resistance or capacitance), a magnetic signal or a metal detector sensing signal.

35 Claims, 8 Drawing Sheets

ELECTROTRANSPORT DEVICE AND METHOD OF SETTING OUTPUT

TECHNICAL FIELD

The present invention relates to delivery of therapeutic agents through a body surface by electrotransport. More particularly, the invention relates to a two-part electrotransport delivery device comprised of an electronic controller adapted to be coupled to, one at a time, a plurality of therapeutic agent (eg, drug) containing units.

BACKGROUND ART

The transdermal delivery of drugs, by diffusion through the epidermis, offers improvements over more traditional delivery methods, such as subcutaneous injections and oral delivery. Transdermal drug delivery avoids the hepatic first pass effect encountered with oral drug delivery. Transdermal drug delivery also eliminates patient discomfort associated with subcutaneous injections. In addition, transdermal delivery can provide more uniform concentrations of drug in the bloodstream of the patient over time due to the extended controlled delivery profiles of certain types of patches. The term "transdermal" delivery, broadly encompasses the delivery of an agent through a body surface, such as the skin, mucosa, or nails of an animal.

The skin functions as the primary barrier to the transdermal penetration of materials into the body and represents the body's major resistance to the transdermal delivery of therapeutic agents such as drugs. To date, efforts have been focussed on reducing the physical resistance or enhancing the permeability of the skin for the delivery of drug by passive diffusion. Various methods for increasing the rate of transdermal drug flux have been attempted, most notably using chemical flux enhancers.

Others have attempted to increase the rates of transdermal drug delivery using alternative energy sources such as electrical energy and ultrasonic energy. The present invention relates specifically to electrically assisted transdermal delivery, also referred to as electrotransport. The term "electrotransport" as used herein refers generally to the delivery of an agent (eg, a drug) through a membrane, such as skin, mucous membrane, or nails. The delivery is induced or aided by application of an electrical potential. For example, a beneficial therapeutic agent may be introduced into the systemic circulation of a human body by electrotransport delivery through the skin. A widely used electrotransport process, electromigration (also called iontophoresis), involves the electrically induced transport of charged ions. Another type of electrotransport, electroosmosis, involves the flow of a liquid, which liquid contains the agent to be delivered, under the influence of an electric field. Still another type of electrotransport process, electroporation, involves the formation of transiently-existing pores in a biological membrane by the application of an electric field. An agent can be delivered through the pores either passively (ie, without electrical assistance) or actively (ie, under the influence of an electric potential). However, in any given electrotransport process, more than one of these processes, including at least some "passive" diffusion, may be occurring simultaneously to a certain extent. Accordingly, the term "electrotransport", as used herein, should be given its broadest possible interpretation so that it includes the electrically induced or enhanced transport of at least one agent, which may be charged, uncharged, or a mixture thereof, whatever the specific mechanism or mechanisms by which the agent actually is transported.

Electrotransport devices use at least two electrodes that are in electrical contact with some portion of the skin, nails, mucous membrane, or other surface of the body. One electrode, commonly called the "donor" electrode, is the electrode from which the agent is delivered into the body. The other electrode, typically termed the "counter" electrode, serves to close the electrical circuit through the body. For example, if the agent to be delivered is positively charged, ie, a cation, then the anode is the donor electrode, while the cathode is the counter electrode which serves to complete the circuit. Alternatively, if an agent is negatively charged, ie, an anion, the cathode is the donor electrode and the anode is the counter electrode. Additionally, both the anode and cathode may be considered donor electrodes if both anionic and cationic agent ions, or if uncharged dissolved agents, are to be delivered.

Furthermore, electrotransport delivery systems generally require at least one reservoir or source of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically at any one time, one pole of the power source is electrically connected to the donor electrode, while the opposite pole is electrically connected to the counter electrode. Since it has been shown that the rate of electrotransport drug delivery is approximately proportional to the electric current applied by the device, many electrotransport devices typically have an electrical controller that controls the voltage and/or current applied through the electrodes, thereby regulating the rate of drug delivery. These control circuits use a variety of electrical components to control the amplitude, polarity, timing, waveform shape, etc. of the electric current and/or voltage supplied by the power source. See, for example, McNichols et al U.S. Pat. No 5,047,007.

To date, commercial transdermal electrotransport drug delivery devices (eg, the Phoresor, sold by Iomed, Inc. of Salt Lake City, Utah; the Dupel Iontophoresis System sold by Empi, Inc. of St. Paul, Minn.; the Webster Sweat Inducer, model 3600, sold by Wescor, Inc. of Logan, Utah) have generally utilized a desk-top electrical power supply unit and a pair of skin contacting electrodes. The donor electrode contains a drug solution while the counter electrode contains a solution of a bio-compatible electrolyte salt. The power supply unit has electrical controls for adjusting the amount of electrical current applied through the electrodes. The "satellite" electrodes are connected to the electrical power supply unit by long (eg, 1–2 meters) electrically conductive wires or cables. The wire connections are subject to disconnection and limit the patient's movement and mobility. Wires between electrodes and controls may also be annoying or uncomfortable to the patient. Other examples of desk-top electrical power supply units which use "satellite" electrode assemblies are disclosed in Jacobsen et al U.S. Pat. No. 4,141,359 (see FIGS. 3 and 4); LaPrade U.S. Pat. No. 5,006,108 (see FIG. 9); and Maurer et al U.S. Pat. No. 5,254,081

More recently, small self-contained electrotransport delivery devices adapted to be worn on the skin, sometimes unobtrusively under clothing, for extended periods of time have been proposed. Such small self-contained electrotransport delivery devices are disclosed for example in Tapper, U.S. Pat. No. 5,224,927; Sibalis, et al U.S. Pat. No. 5,224,928; and Haynes et al U.S. Pat. No. 5,246,418.

There have recently been suggestions to utilize electrotransport devices having a reusable controller which is adapted to by used with multiple drug-containing units. The drug-containing units are simply disconnected from the controller when the drug becomes depleted and a fresh drug-containing unit is thereafter connected to the controller. In this way, the relatively more expensive hardware components of the device (eg, batteries, LED's, circuit hardware, etc) can be contained within the reusable controller, and the relatively less expensive donor reservoir and counter reservoir matrices can be contained in the single use/disposable drug-containing unit thereby bringing down the overall cost of electrotransport drug delivery. Examples of electrotransport devices comprised of a reusable controller adapted to be removably connected to a drug-containing unit are disclosed in Sage, Jr. et al, U.S. Pat. No. 5,320,597; Sibalis, U.S. Pat. No. 5,358,483; Sibalis et al, U.S. Pat. No. 5,135,479 (FIG. 12); and Devane et al UK Patent Application 2 239 803. The Devane Application discloses a two-part electrotransport system comprised of a controller and a drug-containing unit. The two parts are electrically and mechanically coupled to form a complete electrotransport device. One of the Devane devices has cooperating electrical contacts on the controller and drug unit, specifically projections on the drug unit engage microswitches on the controller, to select a given therapeutic program/electrotransport current. Another of the Devane electrotransport devices has a bar code on the drug unit which can presumably be scanned by a scanner in the controller (eg, by passing the scanner over the bar code) to signal the controller the type of drug-containing unit that is being connected thereto.

DISCLOSURE OF THE INVENTION

It is an aspect of the invention to provide a two-part electrotransport delivery device, the device having an electronic controller with a plurality of predetermined electronic outputs (eg, electric current and/or voltage outputs), which controller is adapted to be coupled to a plurality of different therapeutic agent-containing units, one at a time, for administering the therapeutic agent through a body surface (eg, skin) by electrotransport.

It is a further aspect of the present invention to provide a reliable means for signaling to the electronic controller the particular type of therapeutic agent-containing unit which is being coupled thereto and for selecting a specific controller output which is suited for the coupled unit in order to achieve a predetermined therapeutic agent delivery regimen.

The present invention i s directed to a two-part electrotransport device for delivering a therapeutic agent. The first part of the device is an electronic controller which is adapted to be coupled (ie, mechanically and electrically connected) to a plurality of different therapeutic agent-containing units, one at a time. For example, the "different" therapeutic agent-containing units may contain different therapeutic agents (ie, different drugs), different concentrations of the same drug/therapeutic agent, or different loadings (ie, amounts) of the same drug/therapeutic agent.

The controller is capable of providing one of a plurality of different electrical outputs to any particular therapeutic agent-containing unit that is coupled thereto. The number and type of "different" electrical outputs will depend in large part on the different types of therapeutic agent-containing units which are adapted to be used with the controller. For example, the controller could be adapted to be used with (ie, coupled to) two different drug units, one unit containing a narcotic analgesic drug for treating chronic pain and the other unit containing an anti-migraine drug for treating a migraine headache. In such a device, the controller would be designed to have two different electrical outputs. In connection with the narcotic analgesic-containing unit, the controller applies electrotransport current over a relatively extended period of time (eg, 24 hours) to (eg, continuously) administer the narcotic analgesic to treat the chronic pain. In connection with the anti-migraine drug-containing unit, the controller applies electrotransport current over a relatively short (eg, 30 minutes or less) period of time at the onset of a migraine attack. In addition to the timing of the applied electrotransport currents being different in the two above-exemplified examples, the magnitude, polarity, waveform shape (eg, whether pulsed or constant DC), etc, of the applied electrotransport current and/or voltage may also be different between the two different applications (ie, narcotic analgesic for treating chronic pain and the anti-migraine for treating migraine headaches).

Another example of different drug-containing units and different controller outputs concerns an electrotransport controller adapted to be used to deliver a single drug at multiple dosing rates. One example of this mode of operation is an electrotransport device for delivering a narcotic analgesic drug to control chronic and/or acute pain. When delivering analgesics to control pain, it is not unusual to provide different dosing levels for different patients. For example, adult patients typically require higher doses of analgesic that children in order to achieve the same level of analgesia. Also, analgesic drug-tolerant patients typically require higher doses than patients who are not drug tolerant. Thus, the controller is designed to apply electrotransport currents of different magnitudes, one output current having a higher magnitude to deliver a higher dose of analgesic drug compared to an output current having a lower magnitude for delivering a lower dose of analgesic drug.

In all of the above-described examples where the controller has a plurality of different outputs and is adapted to be connected to one of a plurality of different drug-containing units, the output of the controller must be reliable set to meet the needs of the particular therapeutic agent-containing unit which is coupled thereto. In accordance with this invention, the therapeutic agent-containing unit provides a signal to the controller. The signal is received by the controller and the output of the controller is selected in accordance with the received signal in order to appropriately match the controller output to the coupled therapeutic agent-containing unit. The selection of the controller output is accomplished automatically without the need for any manual setting or other human intervention. Thus, the controller output can be reset simply by having the patient or medical technician couple the particular drug unit to the controller, without the need to take any other action.

In one embodiment of the invention, the signal provided by the therapeutic agent-containing unit to the controller is an optical signal comprised of light reflected from a light reflective surface on the drug unit. The light reflective surface is provided with one of a plurality of different reflectivities which can be read by an optical sensor in the controller. The light reflective surface and the optical sensor are aligned when the therapeutic agent-containing unit and the controller are coupled. The optical sensor provides a control signal which sets the output of the controller responsive to the level of reflected light.

In another embodiment of the present invention, the signal provided by the selected therapeutic agent-containing unit to the controller is an electrical resistance signal. The controller applies a test current through the resistor in the drug unit when the controller and the unit are coupled together. The resistance value of (ie, voltage drop across) the resistor is sensed by the controller which then sets its output responsive to the sensed resistance signal.

In another embodiment of the present invention, the signal provided by the selected therapeutic agent-containing unit to the controller is an electrical capacitance signal. The controller has a capacitance sensor which receives the capacitance signal upon the controller and the unit being coupled together. The capacitance sensor provides a control signal which sets the output of the controller responsive to the received capacitance signal.

In still another embodiment of the present invention, the signal is provided by a an electromechanical connector which connects when the controller and the therapeutic agent-containing unit are coupled together. The electromechanical connector is comprised of two parts, a "universal" part on the controller and a "unit-specific" part on the therapeutic agent-containing unit. Thus, the unit specific part will have one of a plurality of configurations depending upon how many different drug units are adapted to be used with the controller. For example, electromechanical connector may be comprised of a series of male members (eg, posts on the therapeutic agent-containing unit) which are adapted to be inserted in, and make electrical contact with, a corresponding number of female members (eg, sockets on the controller). For example, the controller is designed with a plurality (eg, 4) of sockets, whereas four different therapeutic agent-containing units are designed to carry one, two, three or four posts, respectively. When the selected unit is coupled to the controller, the controller's output is set depending upon the number of posts which are engaged in the four sockets on the controller.

An additional embodiment of the invention uses magnet(s) in the drug unit and a magnetic field sensor (eg, a hall-effect device) in the controller. Another embodiment uses pieces of metal in the drug unit and a metal detector in the controller.

BRIEF DESCRIPTION OF THE DRAWINGS

For a further understanding of the objects and advantages of the present invention, reference is made to the following detailed description, taken in conjunction with the accompanying drawings, in which like parts are given like reference numerals and wherein.

MODES FOR CARRYING OUT THE INVENTION

Figure 1:
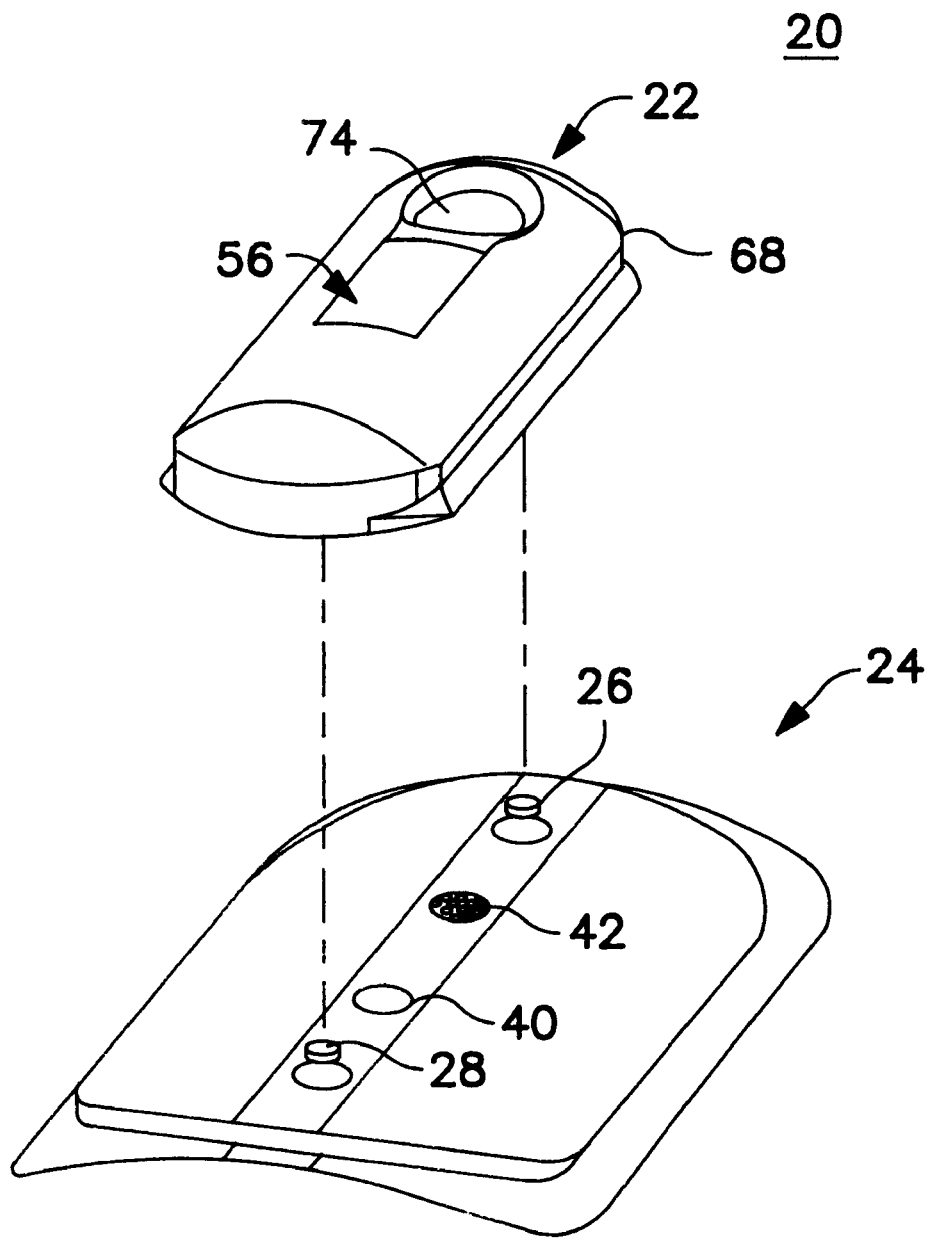
FIG. 1 is a perspective view of an electrotransport device comprised of a reusable controller and a drug-containing unit, in an uncoupled configuration, in which the controller and drug-containing unit communicate by means of an optical signal.

FIG. 1 is a perspective view of electrotransport device 20 having a reusable electronic controller 22 which is adapted to be coupled to and uncoupled from, drug-containing unit 24. The controller 22 is reusable, ie, it is adapted to be used with a plurality of drug units 24, eg, a series of similar and/or very different drug units 24. On the other hand, drug unit 24 typically has a more limited life and is adapted to be discarded after use, ie, when the drug contained therein has been delivered or has been depleted. Thus, after the drug contained in drug unit 24 becomes depleted after a predetermined operational life (eg, 24 hours), the drug unit 24 is uncoupled from the controller 22 and replaced with a fresh drug unit 24 of the same or different structure and/or composition. The controller 22 is designed to provide one of a plurality of different predetermined electrical outputs, which outputs are preferably set at the time the controller is manufactured. The different electrical outputs of the controller 22 are designed to be used with different drug units 24. For purposes of illustration, the controller 22 can be designed to be used with two different drug units 24, both of which units are adapted to be used with the same controller 22 to continuously deliver drug over a period of 12 hours. The two different drug units 24 contain the same drug in their respective donor reservoirs but each contains a different amount of the drug. The drug unit 24 which contains a greater amount of drug is a "high dose" drug unit which is adapted to be used with a higher DC current (eg, 2 mA) output from the controller 22. The drug unit 24 which contains a lesser amount of drug is a "low dose" drug unit which is adapted to be used with a lower DC current (eg, 1 mA) output from the controller 22. Thus, the controller 22 is designed to apply one of two different DC currents (ie, 1 mA or 2 mA) depending upon whether a low dose or a high dose drug unit 24 is coupled thereto. The present invention provides a means for signaling to the controller 22 which type of drug unit (eg, either a high dose or a low dose drug unit) is being coupled thereto and for appropriately setting the output of the controller (ie, setting either the high current output or the low current output) to match the coupled drug unit. In the device illustrated in FIGS. 1 and 2, the drug unit 24 signals the controller 22 by means of an optical signal, which optical signal is automatically sent and then read (ie, decoded) by the controller 22 upon coupling the drug unit 24 thereto (ie, by means of the snap connectors 26, 28). Upon reading the signal, the controller appropriately selects the correct electrical output to apply to the coupled drug unit 24.

Figure 2:
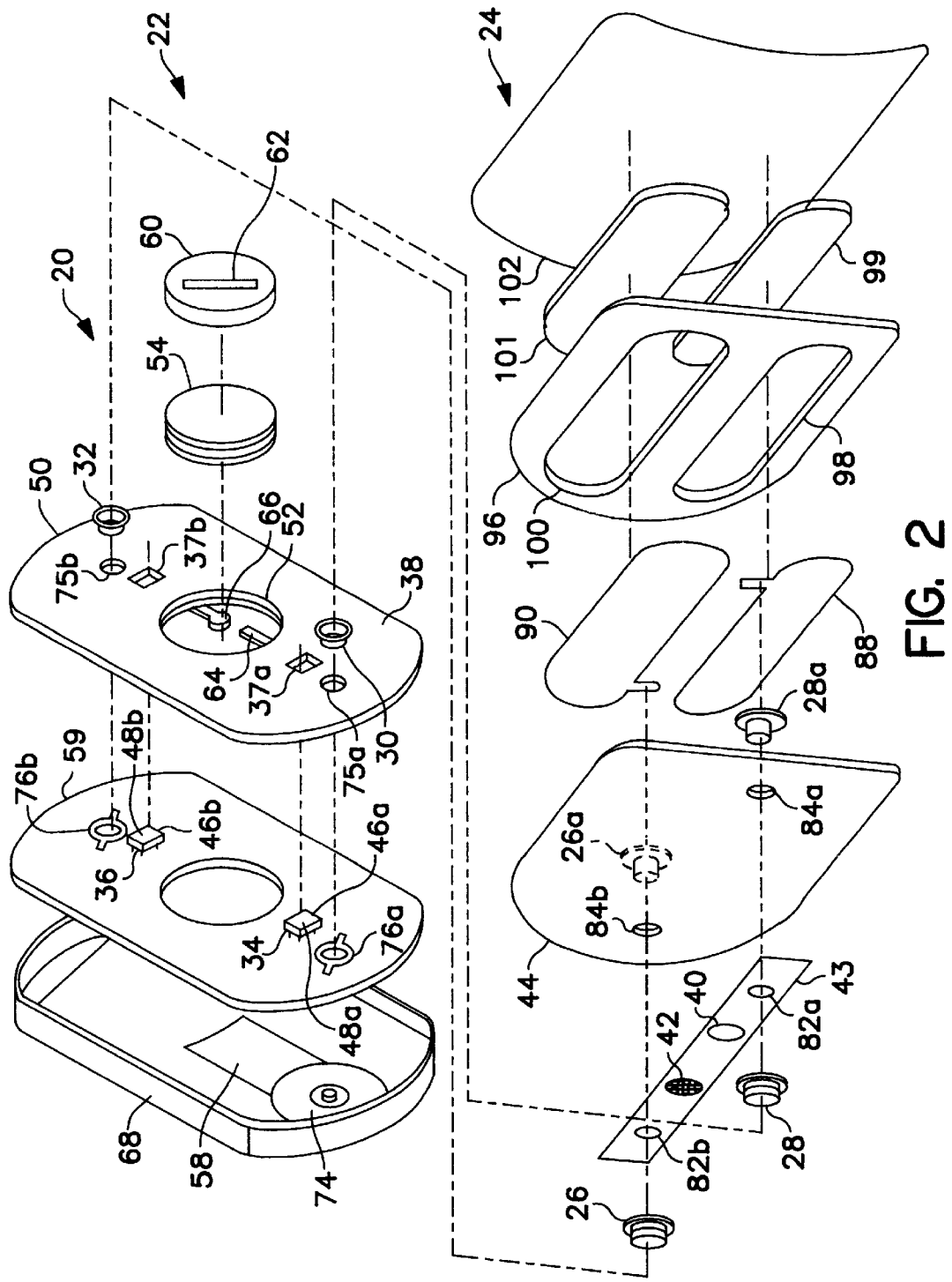
FIG. 2 is an exploded view of the device shown in FIG. 1.

With reference to FIG. 2, there is shown an exploded view of both the drug unit 24 and the controller 22. The controller 22 is comprised of an upper housing 68 and a lower housing 50, both typically formed of a molded plastic such as polypropylene. The upper housing 68 is joined to the lower housing 50 by a contiguous splash proof and preferably water proof peripheral seal. The seal can be made by heat sealing or ultrasonic welding of the joint between housings 50, 68, by gluing the housings together at their common joint using a water proof adhesive, and the like. The lower housing 50 has an opening 52 for receiving the battery 54. Battery contacts 64, 66 are provided to make electrical contact with the respective poles of battery 54. A removable cover 60 screws into the opening 52 to retain the battery 54 in place. The cover 60 has a slot 62 for inserting a coin or a screw driver blade to turn the cover 60 and remove it from the opening 52 in order to access (ie, replace) the battery 54. The controller 22 includes a battery 54, eg a button cell battery, for powering the electrical circuit (not shown) on circuit board 59. The circuit board 59 is formed in a conventional manner, having conductive traces patterned for interconnecting electrical component(s) thereon which control the magnitude, timing, frequency, waveform shape, etc., of the electrical output (eg, voltage and/or current) of controller 22. The conductive traces on circuit board 59 may be deposited with a conventional silk screen printing process or a conventional solder coated copper plated mask and etch process. The insulating substrate of circuit board 59 may be made of standard FR-4 or the like. Although not critical to the invention, controller 22 includes a push button switch 74 which can be used to start operation of device 10 and a liquid crystal display 56 (FIG. 1) which can display, through window 58 (FIG. 2), system information such as the particular type of drug unit 24 that is coupled to the controller, the applied current level, the dosing level, number of doses delivered, elapsed time of current application, battery strength, etc.

The lower housing 50 is provided with holes 75a, 75b which hold electrically conductive receptacles 30, 32. The receptacles 30, 32 protrude through respective holes 75a, 75b in lower housing 50. The ends of receptacles 30, 32 are held in place in by, and make electrical contact with the outputs of the electronic circuit on circuit board 59, by respective conductive gripping fasteners 76a, 76b.

The drug unit 24 is configured to be removably coupled to the controller 22, with the top of drug unit 24 adjacent to and facing the bottom of the controller 22. The top of drug unit 24 is provided with the male parts of two snap type connectors, the male parts being posts 26 and 28 which extend upwardly from drug unit 24. Receptacle 30 is positioned and sized to receive donor post 26 and receptacle 32 is positioned and sized to receive counter post 28. One snap connector pair, for example receptacle 32 and post 28, may be made larger than the other snap connector pair (ie, receptacle 30 and post 26) in order to provide a polarity specific connection of the drug unit 24 to the controller 22. Receptacles 30, 32 and posts 26, 28 are made from an electrically conductive material (eg, a metal such as silver, brass, stainless steel, platinum, gold, nickel, beryllium-copper, etc or a metal coated polymer, eg, ABS with a silver coating). The donor post 26 is electrically connected to the donor electrode 90, which in turn is electrically connected to the donor reservoir 101 which typically contains a solution of the therapeutic agent (eg, a drug salt) to be delivered. The counter post 28 is electrically connected to the counter electrode 88, which in turn is electrically connected to the counter reservoir 99 which typically contains a solution of a biocompatible electrolyte (eg, buffered saline). The electrodes 88 and 90 are typically comprised of electrically conductive materials, most preferably a silver (eg, silver foil or silver powder loaded polymer) anodic electrode and a silver chloride cathodic electrode. The reservoirs 99 and 101 typically include hydrogel matrices which hold the drug or electrolyte solutions and are adapted to be placed in contact with the body surface (eg, skin) of a patient (not shown) when in use. The electrodes 88, 90 and the reservoirs 99, 101 are isolated from each other by foam member 96. The bottom (ie, patient contacting) surface of foam member 96 is preferably coated with a skin contact adhesive in order to secure drug unit 24 on the patient's body. A release liner 102 covers the body contacting surfaces of the two reservoirs 99 and 101 and the adhesive coated surface of foam member 96 before the drug unit 24 is put in use. The release liner 102 is preferably a silicone coated polyester sheet. The release liner 102 is removed when the device 20 is applied to the skin of a patient (not shown).

Thus, the post 26 and the receptacle 30 comprise a snap type connector which electrically connects an output 78a of the circuit on circuit board 59 to the electrode 90 and the reservoir 101. Similarly, the post 28 and the receptacle 32 comprise a snap type connector which electrically connects an output 78b of the circuit on circuit board 59 to the electrode 88 and the reservoir 99. In addition to providing the above described electrical connections, the two snap connectors also provide a separable (ie, not permanent) mechanical connection of the drug unit 24 to the controller 22. Thus, the electrically conductive snap connectors 26, 30 and 28, 32 simultaneously provide the functions of (i) mechanically coupling the drug unit 24 to the connector 22, and (ii) electrically connecting the electrical output of controller 22 to the drug unit 24.

In accordance with this embodiment of the present invention, the drug unit 24 provides an optical signal to the controller 22 in order to properly set the electrical output of the controller to a predetermined output which is appropriate for the specific drug unit 24 and the specific drug contain therein. As is clearly shown in both FIGS. 1 and 2, the mating surface of drug unit 24 has two surface areas 40, 42. Surface area 40 is shown as "white" for high light reflectivity while surface area 42 is shown as "black" for low light reflectivity. Areas 40, 42 may be provided (eg, by printing or painting) directly on the backing layer 44 of drug unit 24 or alternatively on a thin strip of paper or mylar 43 which is mounted on the backing layer 44 by a suitable adhesive.

Controller 22 has a pair of light reflection switches 34, 36 mounted on circuit board 59 and oriented so as to project through holes 37a, 37b in lower housing 50. The switches 34, 36 are directed toward and adjacent to the drug unit 24. The reflective areas 40, 42 are positioned on drug unit 24 such that areas 40, 42 are located closely adjacent to the reflection switches 36, 34, respectively, when the controller 22 and drug unit 24 are coupled.

The light reflection switches 34, 36 are arranged to illuminate the light reflective areas 40, 42 respectively. The reflective areas 40, 42 are arranged such that the illumination from the switch 34 is independently reflected by the area 42 back to the switch 34. Similarly, the illumination from switch 36 is independently reflected by the area 40 back to the switch 36. In a preferred embodiment, the switches 34 and 36 are each provided with a respective illumination source in the form of a photo emitter, 46a and 46b, and a respective matching light sensitive photodetector in the form of a phototransistor, 48a and 48b, such as the SFH901 or SFH902 available from Siemens Optoelectronics Division, Cupertino, Calif. The phototransistors 48a and 48b are connected in a circuit (described below) which generates signals responsive to incident light.

The switches 34, 36 are mounted on the circuit board 59 and respective traces (not shown) by conventional means such as through holes and solder connections. The electrical connections between the circuit board 59 respective conductive traces (not shown) and the photoemitters 46a, 46b and phototransistors 48a, 48b of the switches 34, 36 are explained in detail with reference to FIG. 3, below.

The flexible backing layer 86, which is preferably made of a material (eg, polyethylene sheet) which is impermeable to the passage of liquid water, forms the top-most layer of the drug unit 24. Holes 84a, 84b are provided through the backing layer 44 and perforations 82a, 82b through strip 43 in an aligned arrangement. The conductive base rivets 26a, 28a project through the openings 84a, 84b and the perforations 82a and 82b, respectively, and engage the posts 26, 28 to fix the backing layer 44 therebetween.

Electrodes 88, 90 are composed of electrically conductive materials such as a carbon powder/fiber loaded polymer matrix, a metal powder loaded polymer matrix or a metal foil. Electrodes 88, 90 make contact with the base rivets 26a, 28a. A carbon filled or silver particle filled conductive adhesive is used to bond the electrodes 88, 90 to the base rivets 26a, 28a. The electrodes 88, 90 are in electrical contact with reservoirs 99, 101, respectively. An insulating closed cell foam layer 96 has cavities 98, 100 therein, which cavities contain reservoirs 99, 101, respectively. Typically, one of the reservoirs 99, 101 is the donor reservoir which contains a liquid solution of the therapeutic agent to be delivered by electrotransport while the other is the counter reservoir which contains a solution of a bio-compatible electrolyte (eg, saline). The matrix of reservoirs 99, 101 is preferably a gel.

Transmitting information about the drug unit 24, via the optical signal transmitted to the controller 22, is accomplished by providing the reflective areas 40, 42 with different levels of reflectivity. For example, area 40 may be a standard white having about 90% reflectivity, while area 42 may be a flat black having between about 10 to 15% reflectivity at the wavelength of illumination from the switches 34, 36. With two light reflective surface areas, each area having one of two possible light reflectivities, the drug unit 24 may transmit to controller 22 up to four differently coded optical signals based on the following "reflectivity code"; (1) a first optical signal when both areas 40 and 42 have low reflectivities; (2) a second optical signal when both areas 40 and 42 have high reflectivities; (3) a third optical signal when area 40 has a low reflectivity and area 42 has a high reflectivity; and (4) a fourth optical signal when area 40 has a high reflectivity and area 42 has a low reflectivity. The areas 40, 42 may be encoded by simply painting with a paint having suitable reflectivity. The areas 40, 42 may also be encoded by printing or by applying adhesive tape with suitable reflectivity.

Figure 3:
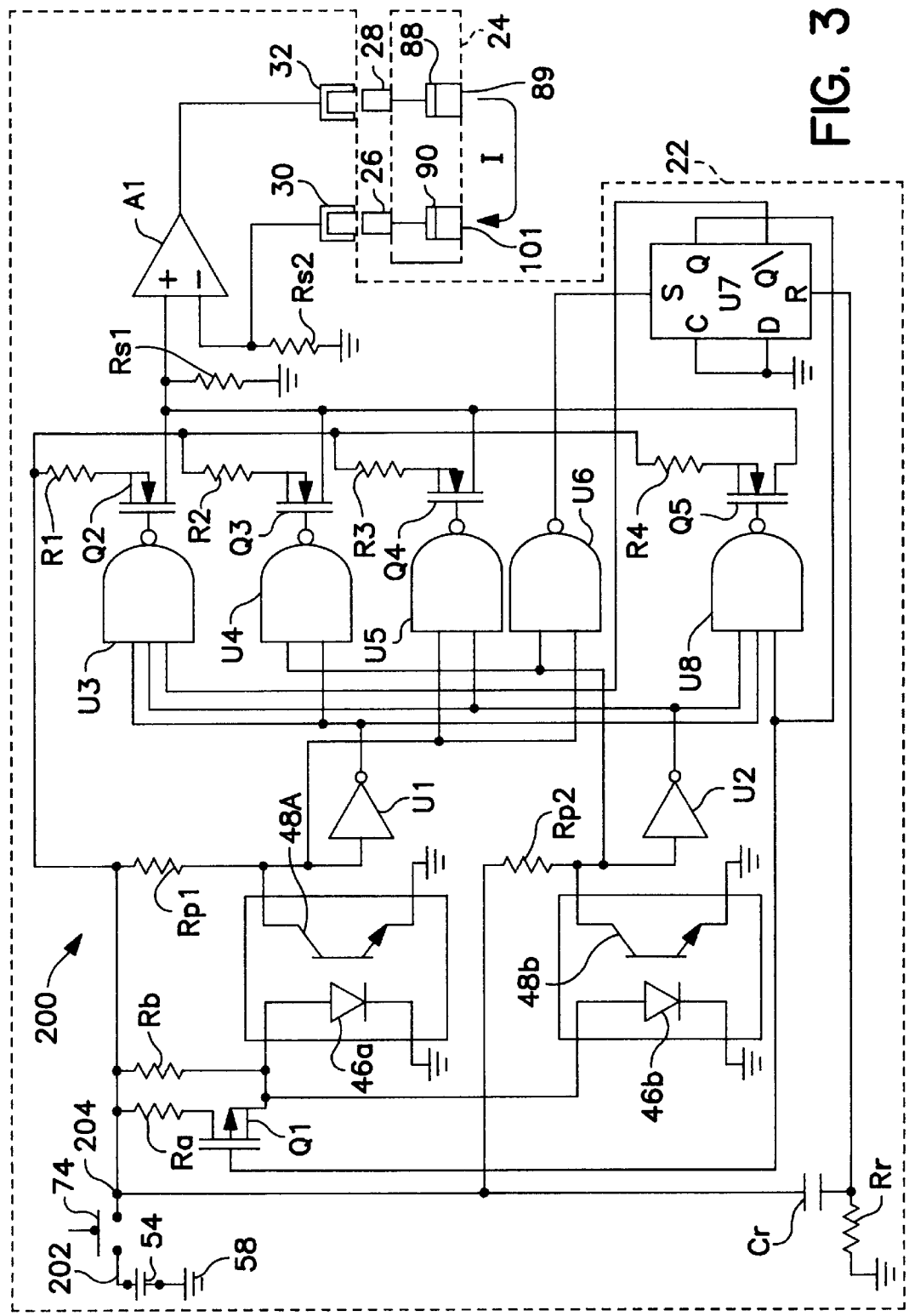
FIG. 3 is a schematic diagram of the optical sensing and control circuit of the device shown in FIGS. 1 and 2.

FIG. 3 is a schematic diagram of one example of an electrical circuit which can be used to read the optical signal provided by drug unit 24 to controller 22 and to decode the signal in order to appropriately set the electrical output of controller 22. Those skilled in the electrical arts will appreciate that other electrical circuits may be used to perform the functions of circuit 200 shown in FIG. 3 and that the details of circuit 200 are shown for purposes of illustration only.

Circuit 200 is carried on the circuit board 59 (shown in FIG. 2) of controller 22. The battery 54 is connected to system ground 58 and by conductive circuit trace 202 to switch 74. When the switch 74 is actuated (ie, closed), the trace 202 is connected to a circuit trace 204. One end of resistors Ra, Rb, Rp1, Rp2 and one terminal of a large capacitor Cr, (eg about 0.1 micro Farad) are connected to trace 204. One end of a large (eg. about 1 meg ohm) resistor Rr is connected to the other terminal of capacitor Cr. The other end of resistor Rr is connected to ground. The resistor Rr and capacitor Cr comprise a circuit to debounce the actuation of the switch 74.

A field effect transistor (FET) Q1 gate is connected to a D-type latch U7 Q output. The FET Q1 drain is connected to the other end of resistor Ra. The FET Q1 source is connected to the anode of photoemitter 46a. The FET Q1, acting as a switch between the FET Q1 drain and source, connects the other end of resistor Ra to the anode of photoemitter 46a when the FET Q1 gate is activated by a high level on the latch U7 Q output. The cathode of photoemitter 46a is connected to system ground. The other end of resistor Rb is connected to the common point of FET Q1 source and the photoemitter anode 46a.

The collector of phototransistor 48a is connected to the other end of resistor Rp1. The collector of phototransistor 48a is also connected to inverter U1 input, to an input of a two input NAND gate U5 and an input of a two input AND gate U6. The emitter of phototransistor 48a is connected to system ground.

The common point of FET Q1 source and the anode of photoemitter 46a are also connected to the anode of photoemitter 46b. The cathode of photoemitter 46b is connected to system ground. The collector of phototransistor 48b is connected to the other end of resistor Rp2, an inverter U2 input, one input of a two input NAND gate U4, and the other input of the two input AND gate U6.

Inverter U2 output is connected to a first input of a three input NAND gate U3, to the other input of the two input NAND gate U5, and a first input of a three input NAND gate U8. Inverter U1 output is connected to the second input of the three input NAND gate U3, the other input of the two input NAND gate U4 and a second input of the three input NAND gate U8. The third input of the three input NAND gate U8 is connected to the U7 latch Q output. The third input of the three input NAND gate U3 is connected to the U7 latch Q\ output.

D latch U7 clock, C, and Data, D, inputs are connected to system ground. The D latch U7 set input, S, is connected to the AND gate U6 output. The D latch U7 reset input, R, is connected to the common point of capacitor Cr and resistor Rr.

The respective NAND gates U3, U4, U5 and U8 outputs drive corresponding P-channel FETs Q2, Q3, Q4, and Q5 gate inputs. The FETs Q2, Q3, Q4, Q5 respective source terminals are connected to one end of a resistor Rs1 and to a non-inverting input of a high gain operational amplifier A1 which functions as a differential amplifier in circuit 200. The other end of resistor Rs1 is connected to system ground.

One end of resistors R1, R2, R3, R4 are connected to a common point at the trace 204. The other end of R4 connects to FET Q5. The other ends of respective resistors R1, R2, R3 and R4 are connected to corresponding P-channel FETs Q2, Q3, Q4, Q5 drain terminals.

The electrode 88 and the reservoir 99 are electrically connected through the mated snap connectors 28, 32, to the amplifier A1 output. The electrode 90 and the reservoir 101 are connected through the mated snap connectors 26, 30, to the inverting input of amplifier A1. One end of a resistor, RS2, is also connected to the inverting input of A1. The amplifier A1 supplies an electrotransport current, I, to the electrodes 88, 90 and the reservoirs 99, 101 based on the action of the circuit 200 as described below.

The circuit 200 operates as follows. After application of the device 20 to the skin, the switch 74 is actuated, connecting circuit trace 202 to trace 204. The connection between traces 202 and 204 causes the battery 54 voltage to be connected to trace 204. The high voltage on trace 204 is momentarily passed through the capacitor C1 to the R input of U7 which causes U7 to reset with the Q output low and the Q\ output high. The low level on the Q output turns off the transistor Q1 thereby disconnecting resistor Ra from the anodes of photoemitters 46a and 46b. The value of Rb is chosen to cause sufficient illumination from the anode of photoemitters 46a such that light reflected from the white area 40 causes the phototransistor 48a to saturate, thereby pulling Rp1, and the input to inverter U1 essentially to system ground, ie a low level. The resistance value of resistor Rb is also chosen to be small enough such that light reflected from the black area 42 will not saturate the phototransistor 48b causing a high level to remain at the input to inverter U2.

A low level on the inverter U1 input and a high level on inverter U2 input cause the inverter U1 output to go high and the inverter U2 output to go low. The NAND gate U4 will have both inputs high, and will therefore turn on transistor Q3. All other NAND gates will remain off, thereby disabling the other FETs Q2, Q4, and Q5. Transistor Q3 connects resistor R2 to the non-inverting input of amplifier A1 and one side of resistor Rs1. Resistors Rs1, Rs2, and level setting resistors R1, R2, R3, and R4 are selected to be much larger than the typical electrical resistance of the body surface (eg, skin) to which the two reservoirs 99, 101 are applied. Human skin resistance is typically in the range of about 5 to 30 kohms.

Since the gain of amplifier A1 is very large, the voltage difference between the non-inverting and the inverting inputs of amplifier A1 will be essentially zero. Resistors Rs1 and R2 will therefore act essentially as a voltage divider with the voltage across resistor Rs1 set by the resistance ratio of resistors R2 and Rs1. The current, I, will flow through the snap connectors 26, 30 and 28, 32, the electrodes 90, 88, the reservoirs 101, 99, and the skin. The current, I, will be the same in the resistor Rs2 since it is the same value as resistor Rs1. The current, I, therefore is determined by the voltage across resistor Rs1 and the voltage from the battery 54. The current delivered by amplifier A1 to the electrodes 88, 90, can therefore be determined by the resistance values of the resistors R1, R2, R3, and R4 relative to the resistance values of resistors Rs1, Rs2, and the reflectivity of the areas 40, 42 on the specific drug unit 24.

Similar logic follows for the case of (i) both areas 40, 42 being white, which selects resistor R1, and (ii) area 40 being black and area 42 being white, which selects resistor R3.

In the event that both the areas 40, 42 are black, neither phototransistor 48a or 48b will saturate causing the respective collectors to both remain high. The inputs to AND gate U6 will be high, causing the output of AND gate U6 and the S input of U7 latch to go high. The latch U7 will be set causing the Q output to go high. The N-channel transistor Q1 will be switched on, connecting the resistor Ra to the anodes of photoemitters 46a and 46b.

The resistor Ra is selected so that illumination from the photoemitters 46a and 46b is sufficient to provide enough light reflected from a black surface areas 40 and 42, to saturate the phototransistors 48a and 48b. The resulting low level on the collectors of phototransistors 48a and 48b will cause a high level to the first and second input of NAND gate U8. The third input of NAND gate U8 will also be high, as it receives the high level from the U7 Q output. The output of NAND gate U8 will go low, thereby turning on P-channel FET Q5. The other NAND gates U3, U4, U5 remain off. Resistor R4 is thereby connected to the non-inverting input of amplifier A1, selecting the current, I, according to the values of resistors R4 and Rs1.

In the event that the switch 74 is activated when no drug unit 24 is coupled to controller 22, no light will be reflected back to the phototransistors 48a, 48b. The voltage at the collectors of phototransistors 48a, 48b will remain high. Again, the AND gate U6 high output will cause the set input S of latch U7 to go high, thereby setting the Q output high. This time however, the first two inputs to NAND gate U8 will be low causing the output of U8 NAND gate to remain high and the P-channel transistor Q5 turned off. The other NAND gates will also be off since at least one input to each NAND gate U3, U4, U5, U8, is low. The amplifier A1 therefore will not be driven to supply current I.

In summary, the circuit 200 selects one of four current setting resistors R1 through R4 for delivering one of four different (ie, different magnitude) DC currents to the electrodes 88, 90 and the reservoirs 99, 101 as a function of the coding combination of white and black on the areas 40 and 42 of drug unit 24.

In other embodiments of the present invention, additional light reflective areas, light reflective switches and additional decoding logic may be provided in the controller 22 and drug unit 24 to select one of a larger number of desired controller outputs.

Although circuit 200 only has the ability to select one of four different constant magnitude DC electrotransport currents based on the optical signal received from the drug unit 24, it should be noted that the outputs of NAND gates U3, U4, U5 and U8 can also be used to select other electrical currents besides a constant DC current. For example, the NAND outputs could select different pulsed DC or AC current generators, or DC current generators having different waveforms (eg, pulsed DC current), duty cycles and the like. Furthermore, the circuit 200 can also be modified to include a mechanism for selecting different time intervals for application of electrotransport current, or repetitive application of a predetermined current according to different therapeutic regimens.

Figure 4:
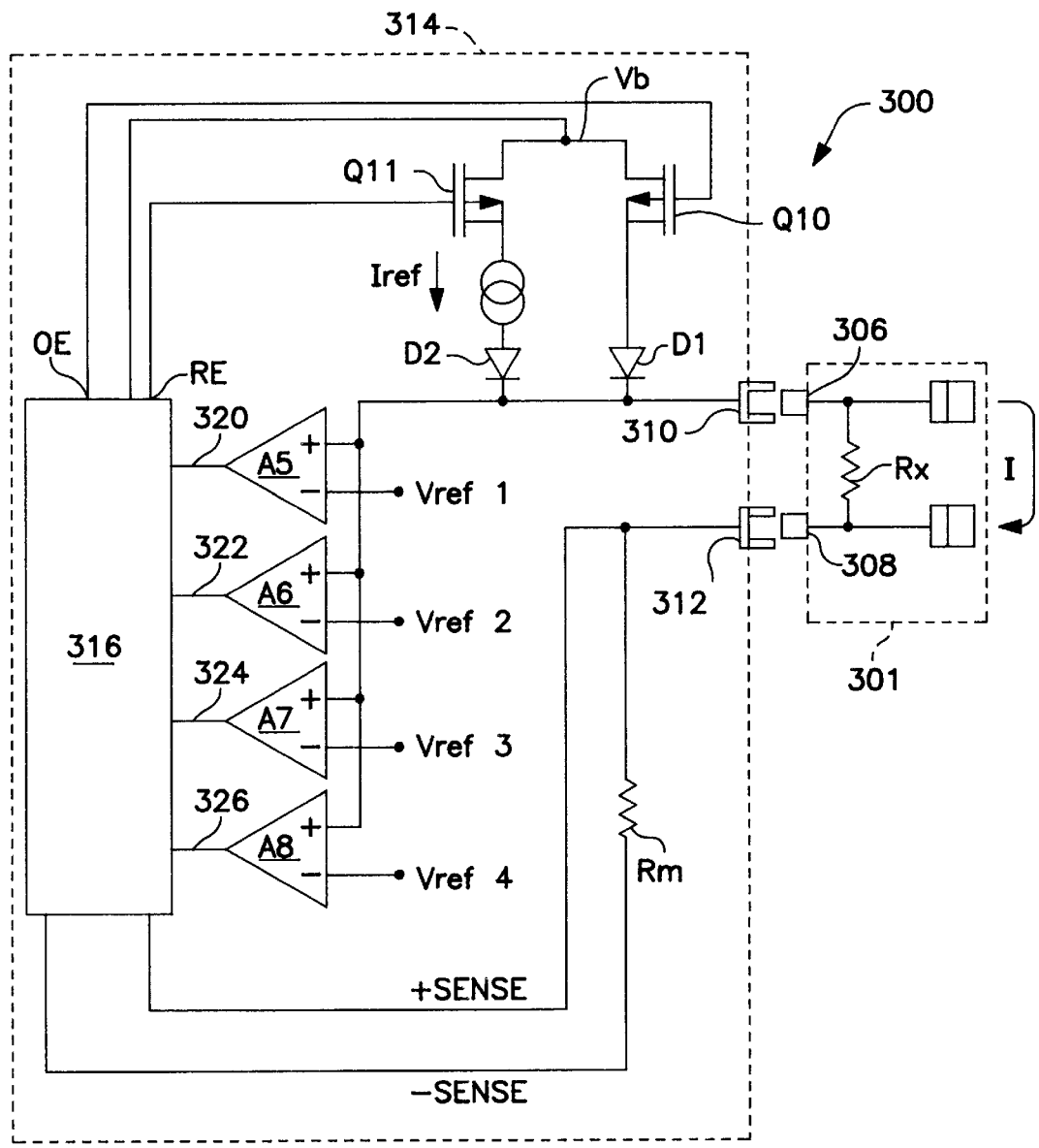
FIG. 4 is a schematic diagram of another two-part electrotransport device having a resistance signal sensing and control circuit.

FIG. 4 illustrates a 2-part electrotransport delivery device 300 comprised of a controller 314 adapted to be coupled to one of a plurality of different drug units 301. Each drug unit 301 provides an electrical signal to the controller 314, the electrical signal being provided by a "test current" which is applied, by the controller 314 through the "identifying resistor" Rx in drug unit 301, when the drug unit 301 is first coupled to the controller 314. A sensing circuit within the controller 314 senses the value of resistor Rx (which resistor has a different resistance value in the different drug units 301) in order to identify which drug unit 301 is being coupled thereto and to appropriately select the one electrical output (of a plurality of electrical outputs) which is matched to the particular drug unit 301.

Similar to device 20 illustrated in FIGS. 1 to 3, device 300 includes a pair of electrically conductive snap connectors 306, 310 and 308, 312 for simultaneously (i) mechanically coupling drug unit 301 to controller 314 and (ii) electrically coupling the electrical output of controller 314 to the drug unit 301.

Drug unit 301 is provided with an identifying resistor Rx connected between the electrode assemblies 302 and 304. The resistance of resistor Rx is chosen to be much larger (eg. at least three times and preferably at least about 20 times) the typical electrical resistance of the body surface (eg, skin) to which the device is adapted to be applied. In the case of human skin, the electrical resistance of human skin is typically in the range of 5 to 15 kohms and hence the resistance of resistor Rx will typically be chosen to be at least about 50 kohms.

The controller 314 includes a current measuring resistor Rm having one end connected to the receptacle 312 and to a very high impedance +sense input of a logic-current control device 316. The +sense input impedance is sufficiently high that no significant current will flow into the +sense input when current is flowing in resistor Rm. The other end of resistor Rm is connected to a low impedance −sense input of the control device 316. The −sense input acts as a current, I, return line for the resistor Rm. The resistance value of resistor Rm is typically a low value relative to the electrical resistance of the animal body surface (eg, 5 to 15 kohm for human skin) to which drug unit 301 is applied. The controller 314 also includes four voltage comparators A5, A6, A7 and A8 each having a plus (+) input, a minus (−) input and a comparator output.

The respective minus input of each comparator A5 through A8 is connected to a corresponding reference voltage Vref1, Vref2, Vref3 and Vref4 and is derived from a voltage divider (not shown) relative to the receptacle 312. Such voltage dividers are well known in the art. The respective plus input of each comparator A5 through A8 is connected to a common point at the receptacle 310. The respective outputs of each comparator A5 through A8 are connected to corresponding logic inputs 320, 322, 324, and 326 of the circuit 316.

The circuit 316 includes a current enable output signal OE, a read enable output signal RE and an output control voltage Vb. The output control voltage Vb is connected to N-channel FETs Q10 and Q11 drain terminals. Signal OE is connected to the FET Q10 gate input and signal RE is connected to the FET Q11 gate input. The FET Q10 source terminal is connected to the anode of blocking diode D1. The FET Q11 source terminal is connected to one terminal of a constant current source, Iref. The other terminal of Iref is connected to the anode of blocking diode D2. The current source Iref provides a known reference current of predetermined value. Iref is typically set to a low value, eg, 1–2 uA, relative to the applied electrotransport drive current I. The cathodes of diodes D1 and D2 are connected to the common point of the plus inputs of comparators A5 through A8 and the receptacle 310.

Circuit 316 operates as follows. Upon coupling the drug unit 301 to the controller 314, but before placing the electrode assemblies 302, 304 on the skin, the circuit 316 is activated. The activation of circuit 316 can be accomplished automatically upon connecting the snap connectors 306, 310 and 308, 312 or manually, for example by the closure of switch 74 on the controller 22. Activation of the circuit 316 initiates a first timing circuit (not shown) that begins a timing period Te. The timing period Te enables a high level voltage Vte on the RE output. The high level Vte on the RE output turns on FET Q11 which connects the current source Iref, to the receptacle 310. The current Iref flows through the snap connector 310, 306, through the resistor Rx (no current Iref flows through the electrode assemblies 302, 304 since the electrode assemblies have not yet been placed on the body of the patient) and returns through the snap connector 308, 312 and the resistor Rm to the low impedance −sense return input of circuit 316.

Voltage developed across Rx by the current Iref is compared to the reference voltages Vref1 through Vref4 by the comparators A5 through A8 during the period Te. One or more of the comparators will output high levels on their respective outputs according to the value of Rx and the value of the corresponding reference voltage, Vref1–Vref4. The circuit 316 decodes the resulting logic inputs 320–326 and provides an amplifier means (not shown) for controlling the signal, Vb. The signal Vb is controlled such that the FET Q11 will deliver the predetermined value of electrotransport drive current, I, according to the value of resistor Rx, when enabled by the signal OE.

After the end of the enable period Te, the electrode assemblies 302, 304 are then placed against the skin of the patient. Upon another activation of the controller 314, for example, by another switch actuation (not shown) or by detecting the change of voltage across the electrode assemblies 302, 304 when the device 300 is placed on the skin, the circuit 316 enables the beginning of an output period, To. At the beginning of time period To, the output signal OE goes high thereby causing the circuit 316 to begin controlling the voltage Vb.

During the output period To, the voltage Vb from the circuit 316 is responsive to the voltage across the resistor Rm as sensed by the +sense and −sense inputs and to the circuit 316. Circuit 316 is provided with suitable negative feed back and gain, when the output signal OE is high, such that Vb is controlled to provide a constant current, I, to flow in the sense resistor Rm, independent over the expected range of the electrical resistance of the skin. The value of current in the resistor Rm will be the same as that flowing through the electrode assemblies 302, 304 and the skin, since they are effectively in series.

Again, although the circuitry which selects and controls the outputs of controller 314 has been shown in terms of selecting one of four alternative constant currents by sensing (ie, decoding) the value of resistor Rx, the circuit 316 may provide other output currents besides constant DC current, including pulsed DC currents, intermittent DC currents, time-varying (ie, non-constant) DC currents, intermittent polarity reversing currents, and even AC currents. Furthermore, additional comparators and control logic may be provided in order to select from an increased number of such alternate currents or waveforms.

Figure 5:
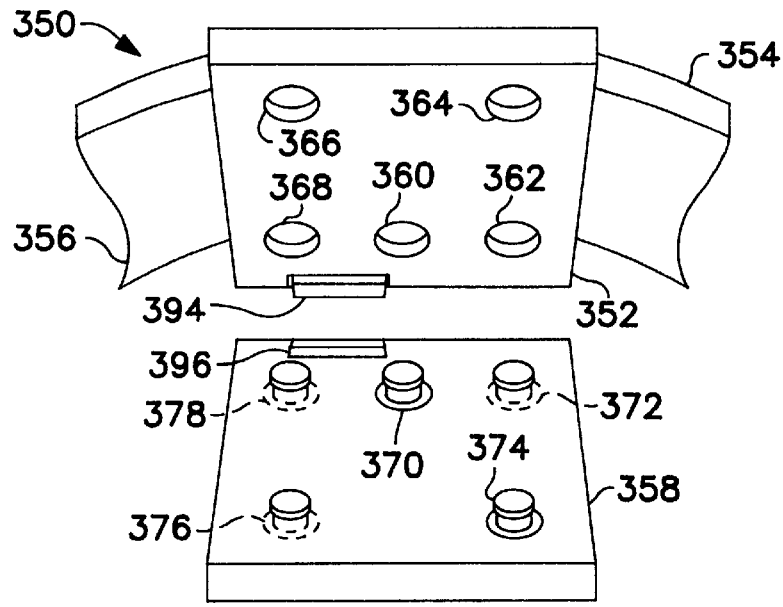
FIG. 5 is a perspective view of another two-part electrotransport device, in which the controller and the drug unit communicate by means of an electro-mechanical connector.
Figure 6:
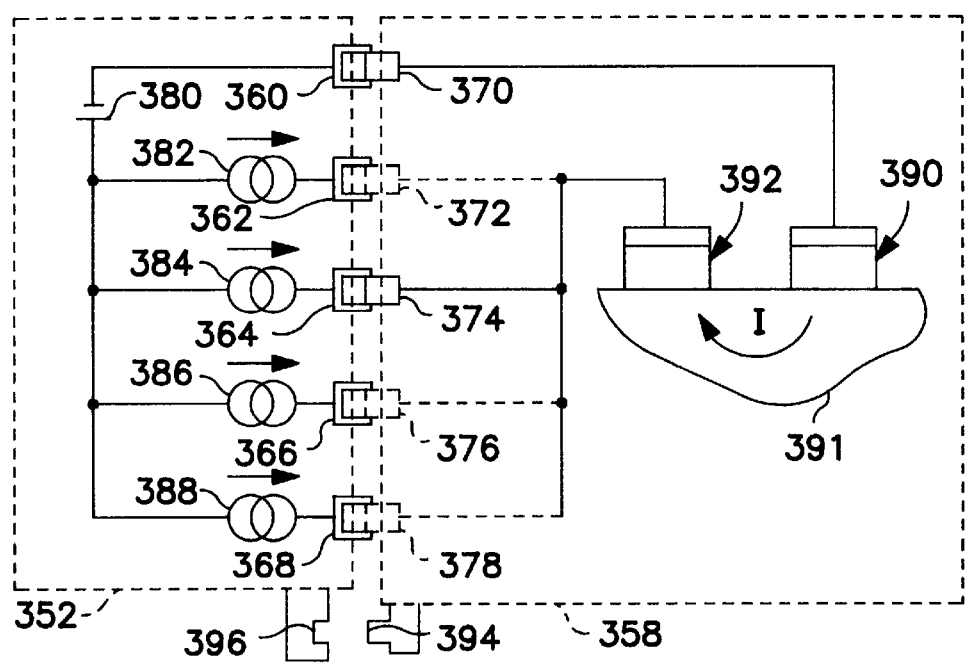
FIG. 6 is a schematic diagram of the signal sensing and control circuit of the device shown in FIG. 5.

FIGS. 5 and 6 illustrate a perspective view of a two-part electrotransport drug delivery device 350 comprised of a controller 352 and a drug unit 358 which are coupled by electromechanical connectors which simultaneously provide mechanical and electrical coupling of the drug unit 358 to the controller 352 and a means for providing a signal to the controller 352 as to the particulars of the drug unit 358 which is being coupled thereto.

The controller 352 has a strap 354, 356 (which strap includes conventional buckle, tongue-and-hole elements, not shown) for attaching device 350 to the limb of a patient for treatment. The body proximal side of controller 352 contains a plurality of electrically conductive receptacles (eg, in the form of female parts of two-part snap connectors) 360, 362, 364, 366 and 368.

The drug delivery unit 358 has a body distal surface with one or more posts 370, 372, 374, 376 and 378 (eg, in the form of male parts of two-part snap connectors) which are positioned to be in alignment with one or more of receptacles 360, 362, 364, 366 and 368, respectively. In the case of the particular drug unit 358 shown in FIG. 5, only posts 370 and 374 are present. Thus, post 370 and receptacle 360 comprise one mating snap connector pair and post 374 and receptacle 364 comprise a second mating snap connector pair. Posts 372, 376 and 378 are not present on the drug unit 358 shown in FIG. 5, although their locations are aligned with receptacles 362, 366 and 368, respectively, on controller 352.

The populated locations of posts 370, 374 and unpopulated post locations 372, 376 and 378 can be seen to comprise a position code. With the five stud/receptacle location pairs, a unique one out of four selection may be made between a reference post/receptacle pair, eg post 370 and receptacle 360, and a second post/receptacle pair, eg post 374, receptacle 364, by populating only one of the other four post locations on the drug unit 358.

When the controller 352 and the drug unit 358 are aligned and mated, post 370 mates with receptacle 360 and post 374 mates with receptacle 364. receptacles 362, 366 and 368 are left unconnected. Different drug units may be made having the second post positioned alternatively in one of the locations 372, 376, or 378.

It is apparent that the posts 370, 374 and receptacles 360, 364 co-act to provide electrical connection and signal encoding means between the controller 352, and the drug unit 358. Optionally, the snap connectors 360, 370 and 364, 374 also provide a mechanical coupling of the drug unit 358 to the controller 352, although the mechanical coupling may be accomplished by other means such as mechanical coupler 394, 396.

FIG. 6 shows a schematic diagram of device 350 with the controller 352 mechanically coupled to the drug unit 358. The controller 352 includes a power source (eg, one or more batteries) 380 and four current control sources 382, 384, 386 and 388. The drug unit includes two electrode assemblies 390, 392, at least one of which contains a therapeutic agent with the other acting as a counter electrode assembly. The electrode assemblies 390, 392 are mounted as before described on the bottom of the delivery unit 358 to make contact with the body surface (eg, skin) 391 of a patient when the device 350 is attached to patient's limb. One terminal of each current control source 382 through 388 is electrically connected to a common terminal of the power source 380, the other terminal of each respective current control source 382 through 388 is electrically connected to the respective receptacle 362 through 368. The other terminal of the power source 380 is electrically connected to the remaining receptacle 360.

When the controller 352 is connected to the drug unit 358, and the device 350 is attached to the patient's limb with the electrode assemblies 390, 392 in contact with the patient's skin 391, a complete electrical circuit is formed by the power source 380, the current control source 384, the snap connector pair 364, 374, the electrode 392, the patient's skin 391, the electrode 390 and the snap connector pair 360, 370. The electrotransport current delivered to the drug unit 358 is therefore selected by the location of the post 374 which mates with receptacle 364 and is thereby controlled by current control source 384 which is electrically connected to the "selected" receptacle 364.

The receptacle 360 acts as a reference point for the system of location coding receptacles and posts. The selection of different control currents specific to drug units having different therapeutic treatment regimens is made by the location of the posts on the drug unit 358. The specific post location 374 provided on the drug unit 358, provides a connection to the receptacle 364 on the controller 352. This particular connection returns a signal to the controller 352, in the form of the current delivered to the drug unit 358 by the current control source 384. The signal, or current returned to the controller 352, is specific to the coupled drug unit 358 and the therapeutic agent contained therein. In the case shown, one of four different control currents may be provided. Device 350 can be modified to have more receptacles connected to different current control sources to provide a greater range of choices for treatment.

In order to avoid mistakes in connection of the controller 352 and drug unit 358, the snap connector pair 360, 370 may have a different size and/or shape from that of the other snap connector pair 364, 374. Alternatively, a cooperating ridge 394 and slot 396 combination or other cooperating guide means on the two connecting units 352, 358 could be provided to prevent mis-orientation. Although device 350 has been explained in regard to snap type connectors, other types of electrically conductive, releasable fastener/connector combinations are contemplated for use in this invention. For example, in place of snap connectors, the controller and drug unit could each hold an array of mechanically interlocking male and female members, respectively, which could be formed of a molded plastic material or the like. The male members (eg, on the drug unit) can be arranged in a pattern which allows the drug unit to be connected to the controller in only one orientation. One or more of the male members (eg, pins) could be coated with an electrically conductive material (eg, silk-screened using a conductive ink). When fitted into the corresponding female members (eg, sockets) in the controller, the pins would complete one or more electrical connections (in a manner similar to that disclosed in FIG. 6) which would comprise a coded signal to be read by the controller. In this case, the code is provided by the particular pin which are coated to be electrically conductive. For example, using an array of 4 pins, each of which can be either coated (ie, conductive) or non-coated (ie, non-conductive), there is a possible 16 (ie, $2^4$) different coded signals which can be configured using the electro-mechanical connector. This electromechanical connector also acts to both mechanically and electrically couple the drug unit to the controller, thereby performing a dual function.

Figure 7:
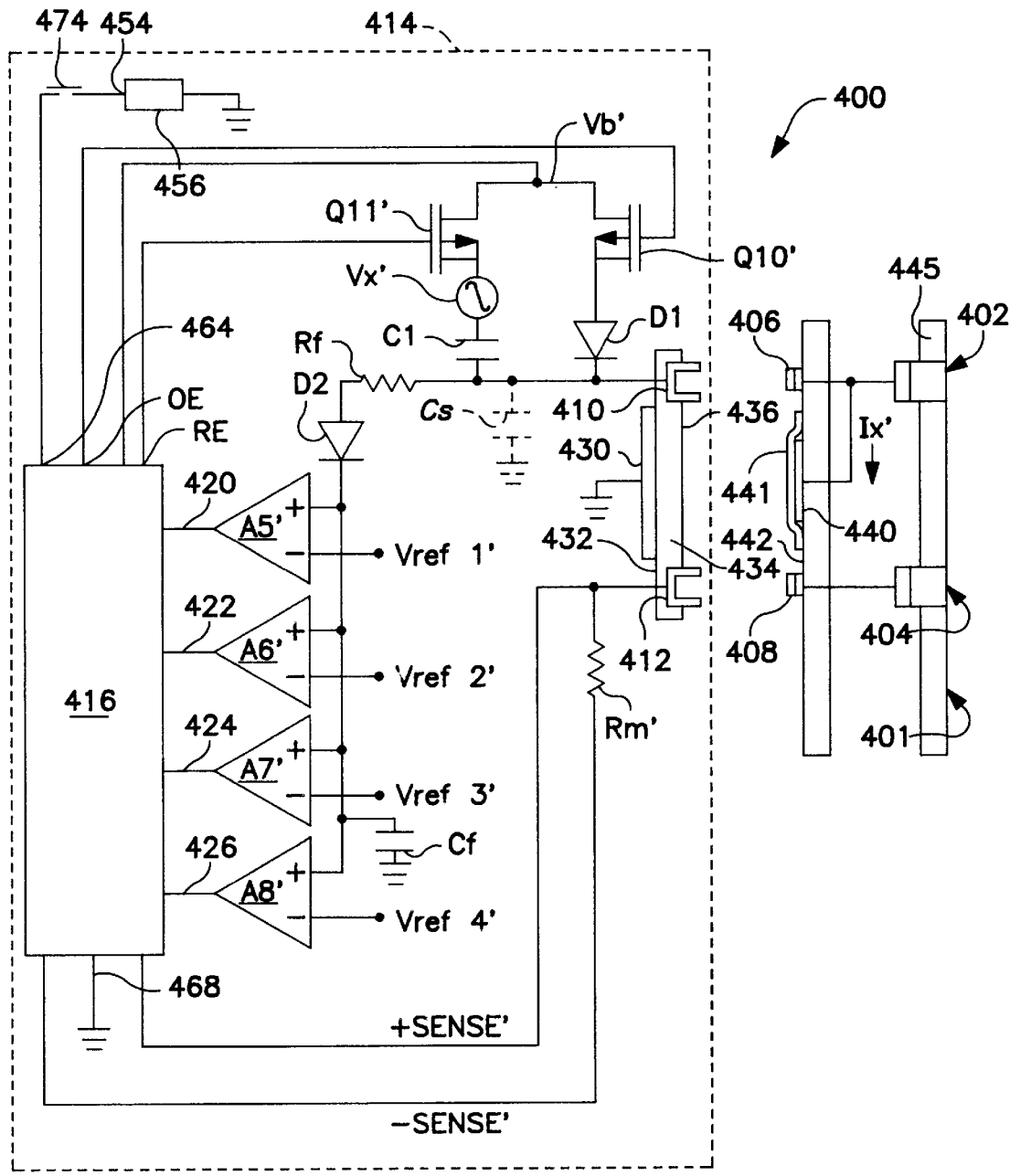
FIG. 7 is a schematic diagram of another two-part electrotransport device in which the controller and drug unit, shown in an uncoupled configuration, communicate by means of a capacitance signal.
Figure 8:
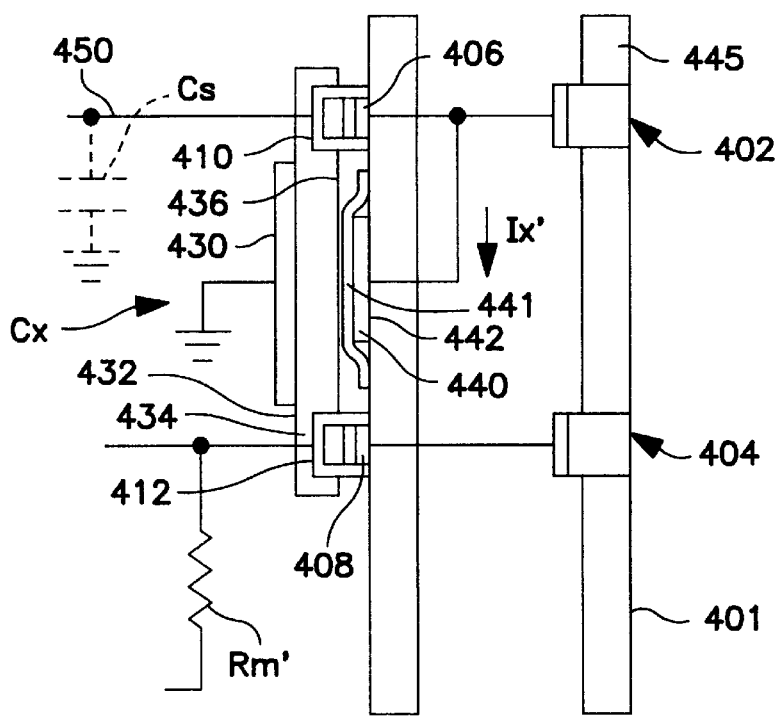
FIG. 8 is a schematic diagram of portions of the deice shown in FIG. 7, with the drug unit coupled to the controller.
Figure 9:
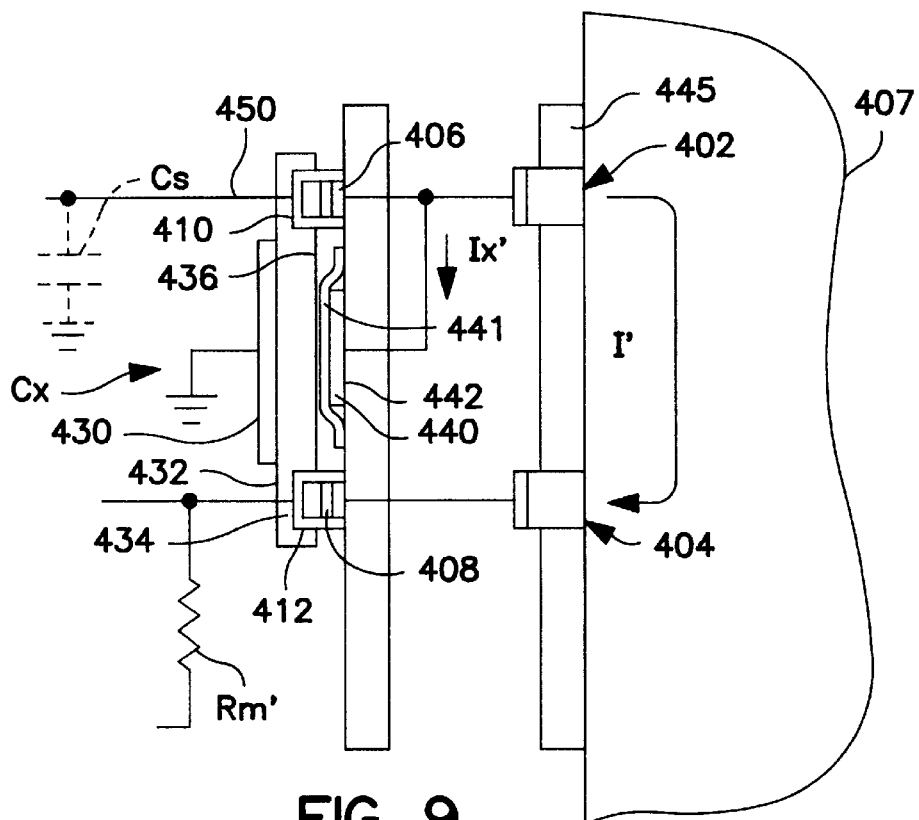
FIG. 9 is a schematic diagram of the same portions of the device shown in FIG. 8, with the drug unit attached to the body surface of a patient; and, FIG. 10 is a schematic diagram of another two-part electrotransport device in which the controller and drug unit communicate by means of a magnetic signal.

FIGS. 7, 8 and 9 all illustrate a 2-part electrotransport delivery device 400 comprised of a controller 414 which is adapted to be coupled to one of a plurality of different drug units 401, one at a time. Each drug unit 401 provides an electrical capacitance signal to the controller 414, the capacitance signal being provided by a capacitor 441, 430 formed when the drug unit 401 is first coupled to the controller 414. When the drug unit 401 is first coupled to the controller 414, a "test current" is applied by the controller 414 through the "identifying capacitor" formed by the parallel plates 430, 441. A sensing circuit within the controller 414 senses the value of the identifying capacitor (which capacitor has a different capacitance value in the different drug units 401) in order to identify which drug unit 401 is being coupled thereto and to appropriately select the one electrical output (of a plurality of electrical outputs) which is matched to the particular drug unit 401. Like the device 20 shown in FIGS. 1 to 3, device 400 includes two snap connector pairs 406, 410 and 408, 412 which function to both mechanically couple the drug unit 401 to the controller 414 and to electrically couple the output of controller 414 to the drug unit 401. Receptacles 410, 412 may optionally be provided with internal peripheral ridges which are configured to removably engage into respective complementary peripheral grooves on the posts 406, 408 when the drug unit 401 is pressed into aligned contact with controller 414. The engaged ridges and grooves thereby mechanically couple the drug unit 401 more securely to the controller 414.

The FIGS. 7, 8 and 9 illustrate the device 400 in three different conditions. FIG. 7 shows the device 400 in an uncoupled configuration, ie, before the drug unit 401 is coupled to the controller 414. FIG. 8 shows the drug unit 401 coupled to the controller 414 but before the device 400 is placed on the patient. FIG. 9 shows the device 400 with the drug unit 401 coupled to the controller 414 and the device 400 applied to the body surface (eg, skin) 407 of a patient and applying an electrotransport drive current I'.

With reference to FIG. 7, there is shown an insulating wall 434 of the control unit 414 which defines planar, parallel, spaced apart internal and external faces 432 and 436. Receptacles 410, 412 are outwardly mounted on the external face 436 of the insulating wall 434. Controller 414 includes a switch 474, a power source (eg, one or more batteries) 456, FET's Q10' and Q11' each having a drain, gate and source terminal, a reference AC voltage source Vx', a reference capacitor C1, a blocking diode D1, a rectifier diode D2, a filter resistor Rf, a sense resistor Rm', a filter capacitor Cf, four threshold comparators A5', A6', A7' and A8' each having a positive (+) compare input, a negative compare (−) input and an output, a logic and current control circuit 416 and four voltage reference sources Vref1', Vref2' Vref3' and Vref4'. The magnitude and frequency of Vx' is typically set to generate a sinusoidal test current (eg, having a frequency of about 10–20 kHz) of suitably low magnitude (eg, about 10–20 μA) relative to the electrotransport drive current, I'.

The circuit 416 includes a current enable output signal OE, a read enable output signal RE, an output control voltage Vb', and an activation input 464 connected to the power source 456 through the switch 474. The opposite pole of the power source 456 is connected to system ground. The circuit 416 is connected to system ground by a return terminal 468. The output control voltage Vb' is connected to N-channel FETs Q10' and Q11' drain terminals. Output enable signal OE is connected to the FET Q10' gate input and read enable signal RE is connected to the FET Q11' gate input. The FET Q10' source terminal is connected to the anode of blocking diode D1. The FET Q11' source terminal is connected to one terminal of the AC voltage source, Vx. The voltage source Vx' provides a known reference voltage of predetermined value. The other terminal of voltage source Vx' is connected to capacitor C1.

The comparators A5' through A8' are high gain, high input impedance threshold detectors which output a high logic level on the respective output when the difference between the respective (+) input and (−) input is positive, otherwise the respective output is a low logic level. The voltage references, Vref1' through Vref4', provide unique reference voltages for each of the comparators A5' through A8', respectively. The voltage references Vref1' through Vref4' are derived from a voltage divider and reference source (not shown) in the controller 414. Voltage reference Vref1' is connected to the (−) input of comparator A5', Vref2' to the (−) input of comparator A6', Vref3' to the (−) input of comparator A7', and Vref4' to the (−) input of comparator A8'. Each positive (+) input of the comparators A5' through A8' are connected to a compare node 452 and to the cathode terminal of rectifier diode D2 and joined to one terminal of the filter capacitor Cf. Each respective output of each comparator A5' through A8' is connected to corresponding logic inputs 420, 422, 424, 426 of the circuit 416. The other terminal of capacitor Cf is connected to system ground. The anode terminal of diode D2 is connected to one end of the filter resistor Rf. The other terminal of filter resistor Rf is connected to a sense terminal 450 formed by the union of one terminal of capacitor C1, the cathode of blocking diode D1 and the receptacle 410.

An AC signal on the sense terminal 450 is peak detected by the diode D2 and filtered by the resistor Rf, capacitor Cf series combination which acts as a low pass filter. The values of resistor Rf and capacitor Cf are arranged such that the AC components of the signal of the sense terminal 450 are essentially attenuated to zero at the frequency of interest, fs, and above, leaving only a DC voltage component at the cathode of diode D2 and the node 452. The DC voltage output at the node 452 will be essentially the peak value of the AC voltage on the terminal 450. For example, a value of about 100 kohm for resistor Rf and a value of about 1 microfarad (uF) for capacitor Cf are suitable for a 6000 to one reduction of AC amplitude for a signal frequency, fs, of about 10 kHz.

The other terminal of capacitor C1 is connected to one terminal of the AC source Vx'. The other terminal of Vx' is connected to the source terminal of FET Q11'. The drain of FET Q11' is connected to a controlled voltage output, Vb', of the circuit 416. The gate of FET Q11' is connected to an enable output, RE, of the circuit 416. The FET Q11' acts as a voltage controlled switch to close the circuit path from Vb' to sense node 450 through the action of a logic high value on the RE enable output as explained further below.

When the RE output is a logic high, the circuit path from Vb' to the node 450 is closed and the AC voltage from Vx' is impressed therein. The capacitor C1, the stray capacitance Cs, and any coupling capacitance (Cx) of the parallel plates 430 and 440, on the node 450 act as a voltage divider according to the relation $$\frac{V_o}{V'x} = C\frac{1}{(C1 + Cs + Cx)}$$

where Cs is the stray capacitance at the node 450, and Cx is the unknown, or added capacitance at the node 450. Therefore, by coupling a predetermined value of capacitance, Cx, to the node 450, the voltage, Vx', can be divided by the predetermined ratio resulting in the AC output voltage $V_o$, on the sense node 450. The AC voltage $V_o$ is peak detected and filtered by the resistor Rf, capacitor CF, diode D2 circuit to yield a DC voltage on the input compare node 452 essentially equal to the peak value of $V_o$. Thus, the controller 414 is signaled according to the value of the coupling capacitance, Cx, which is coupled to the sense node 450. For suitable incremented values of Cx, and suitable values of reference voltages Vx', Vref1' through Vref4', the drug unit 401 signals the controller 414 which unique one of a predetermined set of drug units has been coupled thereto. Circuits for generating such AC and DC reference voltages are well known by those skilled in the art of electronic circuit design.

The drain of FET Q10' also connects to the Vb' output. The gate of FET Q10' is connected to the output enable signal, OE, of the circuit 416. The source of FET Q10' is connected to the anode terminal of the blocking diode D1. The FET Q10' acts as a voltage controlled switch to close the circuit path from Vb' to the sense node 450 through the action of a logic high value on the OE enable output.

Once the unique one of the predetermined set of delivery units 401 has been determined by the control circuit 416, the circuit 416 controls the bias voltage Vb' to control the electrotransport drive current delivered to the drug unit 401 to a predetermined amount. The sequence of the operation of RE and OE signals is similar to that described for the embodiment of FIG. 4.

The signal provided by drug unit 401 to controller 414 is a capacitance signal provided by the coupling capacitor, Cx, formed by electrodes 441 and 430 upon coupling the drug unit 401 to the controller 414. Grounding electrode 430 is disposed on the inside face 432 of the insulating wall 434 of controller 414. The electrode 430 is spaced away from the snap receptacles 410 and 412 sufficiently to minimize effects of stray capacitance. The grounding electrode 430 comprises one half of the coupling capacitor, Cx, (see FIG. 8) formed by mechanically connecting the delivery unit 401 adjacent to the control unit 414 as described below. The grounding electrode 430 is formed by coating a portion of the inside of the wall 434 with an electrically conductive coating, such as silver ink or the like. The electrode 430 may be applied by spraying, brushing, plating, evaporation, plasma deposition or the like.

The physical configuration or circuit layout of the diodes D1, D2, the capacitor C1 and their location relative to the snap receiver 410 are arranged to minimize stray capacitance, represented by the symbol, Cs, with respect to system ground. This minimizes the influence of stray capacitance Cs on the sensitivity of the sense node 450 to changes in capacitance coupled through the snap receptacle 410 and thereby to the change in peak AC voltage at node 450 and to the DC voltage on the compare node 452

The drug unit 401, in addition to the electrode assemblies 402, 404, also contains a coupling electrode 440, and a protective insulating layer 441. The coupling electrode 440 extends laterally over the face 442 to cover a predetermined area, Ac. The coupling electrode 440 is covered with the layer 441 as protection against scratching or inadvertent wear. The layer 441 is preferably made of a thin (eg, about 0.01 mm thickness) sheet material such as cellophane.

Electrode 440 is preferably a thin conductor such as a silver foil adhesively attached to the controller facing side 442 of the drug unit 401. The electrode 440 is electrically connected to the electrode assembly 402 and to the post 406.

Post 406 is electrically connected to electrode assembly 402. Post 408 is electrically connected to the electrode assembly 404. The electrical connection of the posts to the electrode assemblies may be made by conventional means such as wires, deposited or plated conductive traces, conductive adhesives or by overlapping layers of conductive foil, deposited or plated layers. Through holes (not shown) may be provided to connect conductive layers on opposite sides of the insulating wall 442 in the manner shown in FIG. 2.

The two electrode assemblies 402, 404 are spaced apart and insulated from one another by a rear facing insulating wall 445. Wall 445 may have a construction similar to foam layer 96 described earlier and shown in FIG. 2, with cavities for containing the electrode assemblies 402, 404. Alternatively, the wall 445 and wall 442 may be merged into one layer of insulating material having front and rear facing surfaces having cavities for the electrode assemblies and posts. A suitable material for the insulating wall 442 is a closed cell polypropylene foam.

The wall 445 is adapted to hold the electrode assemblies 402, 404 in spaced apart relationship in contact with the skin 407 when the drug unit 401 is attached to the patient's body. The body proximal surface of wall 445 is preferably coated with a skin contact adhesive which can adhere the entire device 400 to the patient's skin.

The coupling electrode 440 is aligned with the studs 406, 408 such that the area, Ac, of the coupling electrode 440 is entirely within the perimeter of the area, Ag, of the grounding electrode 430 when the drug unit 401 is coupled to the controller 414.

The laminated structure of the coupling electrode 440 and protective layer 441 are compressively held in contact with the face 436 of the controller wall 434. The series combination of the grounding electrode 430, the dielectric wall 434, and the laminate of the layer 441 and electrode 440 form the coupling capacitor, Cx. The value of Cx will depend on the thickness and the dielectric constant of the dielectric layers between the two electrodes 430 and 440, and the area Ac of the coupling electrode 440. If the layer 441 is the same for all of the different drug units which are adapted to be coupled to controller 414, then the area, Ac, of the electrode 440 that is on the delivery unit 401, is the only variable which controls the capacitance value of the capacitor Cx. If the area of electrode 440 is halved or doubled, the capacitance, Cx, changes proportionally. Thus the voltage, on the node 450 changes also. The capacitance value of the capacitor Cx, then is $$Cx = A_c \kappa \frac{\varepsilon_0}{t}$$

where κ is the relative dielectric constant of the materials between the electrodes, $\varepsilon_0$ is the permittivity of free space, and t is the thickness of the dielectrics.

For a wall 434 made of closed cell foam polypropylene (dielectric constant of about 2.25) and a thickness of about 1.5 mm (1/16 inch) and an area, Ac of about 0.75 cm², a capacitance of about 1 picofarad (pF) is expected. Thus a range of capacitances, from about 1 to about 8 pF can be obtained with an area, Ac, from about 0.75 to about 6 cm². This range for area Ac is acceptable for small "wearable" electrotransport delivery devices which tend to have skin contact areas in the range of about 10 to 100 cm². The insulating layer 441 is sufficiently thin to have substantially no effect on the value of Cx.

A practical selection of capacitance values for Cx is about 1, 2, 4 and about 8 pF. A practical value for capacitor C1 is about mid-way between the minimum and maximum range of Cx and thus is about 4 pF. Large or smaller values of Cx may be achieved and utilized with the device 400 with advances in the art of fabrication and with the use of other materials. A controller 414 with greater and lesser numbers of detectors may be made to detect more or fewer unique capacitances Cx to provide different alternative therapies.

Device 400 operates as follows. In the uncoupled relationship of FIG. 7, before the controller 414 and the drug unit 401 are connected, no electrical currents flow between the units or from the units to the patients skin. In use, the switch 474 is closed and the power source 456 is connected to an activation input terminal 464 of the control circuit 416.

Activation of the circuit 416 enables an output, RE, which is connected to a gate input of the FET Q11'. The RE output signal turns on the FET Q11' and connects the Vx' AC source in the circuit path from Vb' to node 450. In the absence of the connection of the drug unit 401 to the controller 414, the capacitance on the sense node 450 is only the stray capacitance, Cs. The resulting DC voltage on the compare node 452 is then $$Vc = \frac{V'xC1}{(C1 + Cs + Cx)}$$

The values of Vref1' through Vref4' are chosen so that the circuit 416 remains in the state with RE signal high supplying Vx' to node 450.

With reference to FIG. 8, the drug unit 401 is connected to the controller 414 by engaging the posts 406, 408 with receptacles 410, 412, respectively. When the snap connector pairs 406, 410 and 408, 412 ar connected, the coupling electrode 440 and insulating layer 441 are engaged adjacent to the surface 436 of the wall 434. The coupling capacitance Cx is thereby formed between the sense node 450 and system ground. With the additional coupling capacitance, Cx, in place, the voltage on the compare node 452 drops to $$V'c = \frac{V'xC1}{(C1 + Cs + Cx)}$$

The values of Vref1' through Vref4' and detection logic (not shown) within the circuit 416 are arranged such that the logic circuit 416 detects a condition code specific to the value of Cx which has been connected, stores the condition code in a memory element (not shown), disables the RE logic high, and enables the OE logic output. The time of detection, To, of the condition code may be determined by the elapse of delay time, Te, from an internal timer (not shown) or by detecting the rate of change of voltage, dVc/dt, on the compare node 452 and storing the condition code when dVc/dt is sufficiently small.

The FET Q11' is turned off by the disabled RE output signal and removes the Vx' reference voltage from the circuit path Vb' through FET Q11' and capacitor C1 to node 450. The enabled OE logic output turns on the Q10' FET and connects Vb' through the blocking diode D1 to the node 450. The device 400 is now in an output condition ready to deliver electrotransport drive current through the electrode assemblies 402, 404. The logic circuit 416 controls the value of Vb' and attempts to drive a therapeutic current, I', through the electrode assemblies 402, 404, of the specific coupled drug unit 401. The controller 414 is preprogrammed to supply a specific current to the electrode assemblies depending on the value of the capacitance, Cx, detected. No current will flow, however, until the electrode assemblies 402, 404 are placed in contact with the skin 407, as shown in the FIG. 9.

After the capacitance, Cx, has been detected, a visual or audio display (not shown) may be used to signal to the patient or clinician that the device 400 is ready to be attached to the skin. For example an LED or LCD display 56 (see FIG. 1) may be turned on by the control circuit 416, or an audio annunciator sounded. Alternatively, a fixed delay time may be preprogrammed into the controller 414, allowing the clinician time to attach the connected units 401, 414 to the patient's skin.

Once the electrode assemblies 402, 404 are placed in contact with the skin 407, the preprogrammed current, I', will begin to flow through the patient's skin, carrying the therapeutic agent (which agent is contained in at least one of the two electrode assemblies 402, 404) by electrotransport.

Again, although device 400 has been shown in terms of selecting one of four alternative constant currents by reading (ie, decoding) the value of capacitor Cx, the circuit 416 may provide alternative output current waveforms, such as AC, pulsed and non-constant DC, etc. based on such decoding and selection. Furthermore, additional comparators and control logic may be provided in order to select from an increased number of such alternative currents or waveforms.

Although the capacitive sensing embodiment of device 400 has been described with a coupling capacitor Cx connected between the receptacle 410 and system ground, other connector structures having detectably different capacitive values are contemplated in this invention. For example, The posts 406, 408 may themselves include extended flanges (not shown) of overlapping conductive sheets separated by a thin dielectric layer, in which the capacitance is selected by the area of overlap or thickness of the intervening dielectric.

Alternatively, the coupling capacitor, Cx, may be electrically isolated from the snap connectors 406, 410 and 408, 412, and the detection circuitry and therapeutic current delivery circuit path may be separate paths.

Other known methods of capacitive sensing also may be employed in this invention, including those disclosed in Calvin U.S. Pat. No. 4,345,167; Maier U.S. Pat. No. 4,122,708; Kronberg U.S. Pat. No. 5,135,884; Fudaley U.S. Pat. No. 3,445,835; and Boie et al U.S. Pat. No. 5,337,353.

Another type of signal which can be used in the present invention is a magnetic signal. For example, small magnets can be placed in the drug unit, with different drug units containing magnets of differing magnetic field strengths. The controller contains a magnetic field strength sensing device, such as a Hall-effect device, which are known in the electromagnetic arts. The Hall-effect device senses the strength of the magnetic field produced by the magnet(s) in the drug unit, and sets the controller electrical output according to the sensed magnetic signal.

Figure 10:
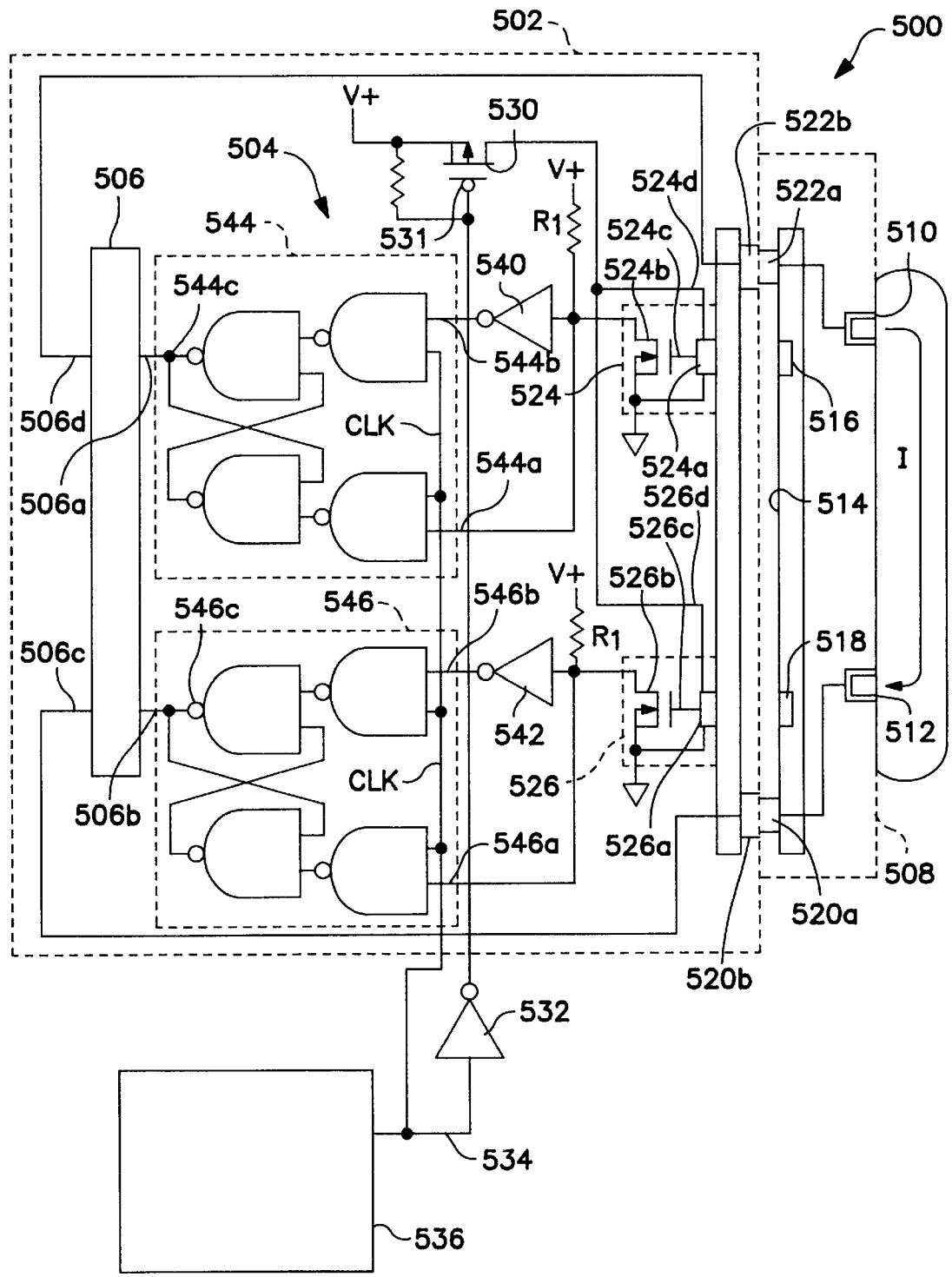

FIG. 10 shows one example of a magnetically actuated electrotransport device 500 comprised of a separable controller 502 and drug unit 508 in accordance with the present invention. The controller 502 contains a sensor and logic circuit 504 and a current control circuit 506. The controller 502 is adapted to be removably coupled to a plurality of disposable drug units 508, one at a time in succession. In use, the device 500 is affixed to the skin of a patient with the electrodes 510, 512 placed in ion-transmitting contact with the skin.

A surface 514 of the drug unit 508 is configured with two spaced apart permanent magnets 516 and 518. Suitable permanent magnets 516, 518 may be formed from a flexible permanent magnetic material known as "PLASTIFORM", part no. B1030, available from Arnold Engineering Company, Norfolk, Nebr., having a thickness of 0.1 cm (0.05 inches), and a length and width of 0.6 cm (0.25 inches). Other permanent magnetic materials may be used in place of magnets 516, 518, such as metallic strips of PERMALLOY (magnetic iron-base alloys containing 45–80% nickel) and the like. The magnets 516, 518 may be attached to or embedded in the surface 514 of the drug unit 508, or may be mounted inside a magnetically transparent covering.

A pair of electrically conductive mechanical snap connectors 520 and 522 are provided to releasably couple, both mechanically and electrically, the drug unit 508 to the controller 502. Snap connectors 520 and 522 are comprised of a post 520a and 522a and a corresponding socket 520b, 522b, respectively. The electrodes 510, 512 in drug unit 508 are electrically connected to the posts 520a, 520b by wires or conductive traces.

The controller 502 contains a pair of magnetically actuated sensor switches 524, 526. The switches 524, 526 are disposed relative to the sockets 520b and 522b such that they are actuated by the permanent magnets 516, 518 when the snap connectors are mechanically coupled. Suitable magnetic sensor switches 524, 526 are the "UNIPOLAR HALL EFFECT" switches, SS141A, available from Honeywell Microswitch Division, Freeport, Ill. The switches 524, 526 each contain a Hall effect sensor element 524a and 526a and an N-channel transistor switch 524b and 526b, respectively. The sensor elements 524a and 526a each have a common terminal connected to the respective source terminals of transistors 524b and 526b, respectively, which are connected to system ground of the controller 502. The elements 524a and 526a also have respective bias terminals 524d and 526d and output terminals 524c and 526c. The output terminals 524c and 526c are connected to respective gate terminals of transistors 524b and 526b.

A pull-up resistor, R1, is connected from the drain of each transistor 524b, 526b to a power source, eg such as a battery (not shown), in the controller 502, which provides system power, V+.

A P-channel transistor 530 has a drain terminal connected to the bias output terminals 524c and 526c. The power supply provides system power, V+, to the source of the transistor 530. The transistor 530 has an active low gate terminal 531 connected to an inverting output of an inverter 532.

The transistor 530 is sized such that, when the transistor gate 531 is pulled low, bias currents will flow in the Hall effect elements 524a and 526a. The bias currents are selected such that, when the elements 524a and 524b are close to a sufficiently intense magnetic field, the elements 524a and 524b send output signals on terminals 524c and 526c sufficient to switch on the transistors 524b and 526b.

Inverter 532 has an input connected to an output 534 of a low duty cycle pulse timer 536.

Set/Rest flip-flops 544 and 546 have active high clock inputs, CLK, connected to the timer output 534.

Drain terminals 524b and 526b are connected to inputs of logic inverters 540 and 542 respectively, and also connected to respective reset inputs 544a and 546a of S-R flip-flops 544 and 546. Inverter output 540 is connected to set input 544b of flip-flop 544. Inverter output 542 is connected to set input 546b of flip-flop 546. Flip-flop outputs 544c and 546c are connected to logic inputs 506a and 506b of the current control circuit 506.

The current control circuit 506 has outputs 506c and 506d electrically connected to the sockets 520b and 522b, respectively. The current control circuit 506 delivers an electrotransport current, I, through the outputs 506c and 506d, the coupled snap connectors 520 and 522, electrodes 510, 512 and through the body of the patient when activated by the logic inputs 506a and 506b.

The magnitude of the current I is controlled by the circuit 506 as a function of logic levels A, B (not shown in FIG. 10) at the inputs 506a, 506b.

The size, shape, spacing and location of the magnets 516, 518 are configured such that, with the snap connectors 520 and 522 coupled, the Hall effect elements 524a and 526a are actuated by the magnetic field provided by the proximity of the elements 524a, 526a to the magnets 516, 518 as described below.

Operation of the device 500 is as follows. The disposable drug unit 508 is attached to the skin of a patient in the conventional manner, eg with straps or adhesives, such that the electrodes 510, 512 are in suitable contact for electrotransport of the therapeutic agent or agents contained in at least one of the electrodes 510, 512.

The controller 502 is activated, for example, by a switch (not shown) and electrical power, eg V+, is supplied to the circuit elements therein. The timer circuit 536 is arranged to output at least one positive going, low duty cycle pulse on the output 534. At each high level on output 534, the CLK inputs of the flip-flops 544, 546 are enabled, such that the logic state on the SR inputs 544a, 544b and 546a, 546b are transferred to the outputs 544c and 546c.

The output of inverter 532 goes low at this time, causing the p-channel device 530 to supply bias current to the Hall effect elements 524a and 526a. In the presence of a sufficiently strong magnetic field, supplied by the magnets 516 and 518, the Hall effect element outputs 524c and 526c go high and turn on the transistors 524b, 526b. When transistors 524b, 526b turn on, the inputs to inverters 540 and 542 go low and apply a low level to the reset inputs 544a and 546a. The inverter 540 and 542 outputs transfer the opposite logic level to the SR flip-flop set inputs 544b and 546b. The flip-flops 544, 546 will remain in that state indefinitely, holding the control inputs 506a and 506b in the state determined by the detection of presence or absence of the magnets 516, 518.

Table I shows the relation between the presence (designated by "yes" and "1" in Table 1) or absence (designated by "none" and "0" in Table 1) of magnets 516, 518, the logic levels output at points A, B and several exemplary current levels which can be delivered by the circuit 506.

TABLE I

| 516 | 518 | A/506a | B/506b | current |
|---|---|---|---|---|
| none | none | 0 | 0 | 50 µA |
| yes | none | 1 | 0 | 100 µA |
| none | yes | 0 | 1 | 150 µA |
| yes | yes | 1 | 1 | 200 µA |

The details of the circuitry for outputting different values of current under control of one of a set of logic levels or for generating narrow pulse width, low duty cycle pulses is known by those skilled in the art.

In other embodiments of this invention, additional magnets and sensors can be provided to increase the range of selectable currents, or for other control functions. As an example, an additional pair of magnets similarly coupled to magnetic sensors connected to a current control circuit, can provide control over the timing or duration of therapeutic current delivery.

Still another type of signal which can be used in the present invention is a signal which can be sensed by a metal detector. For example, small pieces of metal can be placed in the drug unit, with different drug units containing different metals or differing amounts of the same metal. The controller contains a metal detector, which are known in the electromagnetic arts. The metal detector senses the signal produced by the metal(s) in the drug unit, and sets the controller electrical output according to the sensed signal.

While the foregoing detailed description has described several embodiments in accordance with this invention, it is to be understood that the above description is illustrative only and not limiting of the disclosed invention. It will be appreciated that it is possible to modify the type, location and number of mechanical fasteners, and electrical connectors, the materials, shape and form of the controller and drug unit or to include or exclude various elements within the scope and spirit of this invention. Thus the invention is limited only by the claims as set forth below.

We claim:

1. An electrotransport delivery device comprising a therapeutic agent-containing unit having a reservoir containing the therapeutic agent to be delivered, a controller for controlling electrotransport delivery of the agent, a coupler for separably coupling the controller and the therapeutic agent-containing unit, the coupler providing electrical connection between the controller and the therapeutic agent-containing unit, the therapeutic agent-containing unit comprising a predetermined therapeutic agent delivery regimen signaling mechanism which provides a delivery regimen signal to the controller, said controller capable of generating one of a plurality of predetermined outputs corresponding to a plurality of delivery regimens for said agent and further comprising a receiver for receiving the delivery regimen signal and setting one output selected from said plurality of outputs in response to the delivery regimen signal, wherein the device is adapted to deliver said agent according to the selected delivery regimen which is determined by selection of a therapeutic agent-containing unit providing the corresponding delivery regimen signal.

2. The device of claim 1, wherein the delivery regimen signal includes an optical signal.

3. The device of claim 2, wherein the optical signal comprises light reflected from a light reflective surface (40, 42).

4. The device of claim 3, wherein the controller (22) includes a light source (46) and the therapeutic agent-containing unit (24) includes the light reflective surface (40, 42), the light source (46) and the light reflective surface (40, 42) being relatively positioned such that light from the light source (46) illuminates the light reflective surface (40, 42) when the controller (22) is coupled to the unit (24).

5. The device of claim 3, wherein the light reflective surface (40, 42) includes one of a plurality of reflectivities.

6. The device of claim 3, wherein the therapeutic agent-containing unit (24) includes the light reflective surface (40, 42).

7. The device of claim 4, wherein the controller (22) includes an optical sensor (48) adapted to sense the reflected light.

8. The device of claim 7, wherein the optical sensor (48) is adapted to provide a sensor signal responsive to the intensity of the reflected light.

9. The device of claim 7, wherein the coupler (26, 30 and 28, 32) is adapted to align the optical sensor (48) with the reflective surface (40, 42).

10. The device of claim 1, wherein the controller (22) includes a capacitance sensor (414) adapted to sense a capacitance signal (440, 441, 430) provided at least partially by the therapeutic agent-containing unit (401).

11. The device of claim 1, wherein the signal includes an electro-mechanical connector (360, 370, 362, 372, etc.) adapted to send a coded signal and adapted to mechanically and electrically couple the unit (358) to the controller (352).

12. The device of claim 1, wherein the signal comprises an electrical resistance signal (Rx), and wherein a portion of the contacts (370, 374) make electrical connection between the controller (314) and the unit (301).

13. The device of claim 1, wherein the signal is a magnetic field signal.

14. The device of claim 13, wherein the signal is produced by a magnet (516, 518) in the drug unit (508).

15. The device of claim 1, wherein the signal is produced by a metal in the drug unit, and wherein the signal is sensed by a metal detector in the controller.

16. The device of claim 1 wherein the signal is related to one or more parameters selected from the consisting of the type of agent in the unit, the amount of agent in the unit, the concentration agent in the unit, the maximum rate of agent delivery, the maximum overall time that the agent may be delivered, the maximum time per hour during which delivery can be made, and the maximum number of delivery periods that can be made.

17. The device of claim 1 wherein the delivery regimen signal comprises at least one set of a magnet and a magnetic sensor wherein one member of each set is attached to the agent-containing unit and the other member of the set is attached to the controller so that when the agent containing unit is coupled to the controller the magnetic sensor is positioned to detect the magnet.

18. A method of setting one electrical output selected from of a plurality of predetermined electrical outputs of a controller adapted to be coupled to one therapeutic agent-containing unit selected from a plurality of therapeutic agent-containing units each of which corresponds to one of a plurality of predetermined therapeutic agent delivery regimens wherein the selected electrical output will implement the corresponding therapeutic agent delivery regimen corresponding to the selected unit, coupling the selected therapeutic agent-containing unit to the controller, the selected therapeutic agent-containing unit adapted to provide a delivery regimen signal to the controller wherein said delivery regimen signal indicates to said controller which one of the plurality of predetermined electrical outputs should be used with the selected therapeutic agent-containing unit; and, setting the output of the controller to one of the plurality of predetermined outputs which corresponds to the delivery regimen signal from the selected therapeutic agent-containing unit.

19. The method of claim 18, wherein the signal is an optical signal.

20. The method of claim 19, wherein the optical signal is light reflected from a light reflective surface (40, 42).

21. The method of claim 20, wherein the light reflective surface (40, 42) includes one of a plurality of reflectivities.

22. The method of claim 21, further including the step of shining a light source (46) on the reflective surface (40, 42).

23. The method of claim 22, further including the step of sensing light reflected from the reflective surface (40, 42) with an optical sensor (48).

24. The method of claim 23, further including the step of providing a sensor signal responsive to the intensity of the reflected light.

25. The method of claim 21, further including the step of aligning the optical sensor (48) with the reflective surface (40, 42) by coupling the controller (22) to the one unit (24).

26. The method of claim 16, wherein the signal is an electrical resistance signal (Rx).

27. The method of claim 16, wherein the signal is a coded signal generated from an electromechanical connector (360, 370, 362, 372, etc.) that mechanically and electrically couples the unit (358) to the controller (352).

28. The method of claim 16, wherein the signal is a magnetic field signal.

29. The method of claim 28, wherein the signal is produced by a magnet (516, 518) in the one unit.

30. The method of claim 16, wherein the signal is produced by a metal in the one unit, and wherein the signal is sensed by a metal detector in the controller.

31. The method of claim 16, wherein the signal is a capacitance signal (440, 441, 430).

32. The method of claim 24, further including the step of sensing the capacitance signal with a capacitance sensor (414).

33. The method of claim 18 wherein the signal is related to one or more parameters selected from the group consisting of the type of agent in the unit, the amount of agent in the unit, the concentration agent in the unit, the maximum rate of agent delivery, the maximum overall time that the agent may be delivered, the maximum time per hour during which delivery can be made, and the maximum number of delivery periods that can be made.

34. The method of claim 18 wherein the delivery regimen signal comprises at least one set of a magnet and a magnetic sensor wherein one member of each set is attached to the agent-containing unit and the other member of the set is attached to the controller so that when the agent containing unit is coupled to the controller the magnetic sensor is positioned to detect the magnet.

35. A kit for electrotransport delivery of an agent comprising:
- a plurality of therapeutic agent-containing units, each unit comprising a reservoir containing the therapeutic agent to be delivered according to one delivery regimen selected from a plurality of predetermined delivery regimens;
- a controller for controlling electrotransport delivery of the agent;
- a coupler for separably coupling the controller and a therapeutic agent-containing unit selected from the plurality of therapeutic agent-containing units, the coupler providing electrical connection between the controller and the selected therapeutic agent-containing unit;
- each of said therapeutic agent containing units comprising a therapeutic agent delivery regimen signaling mechanism which provides a delivery regimen signal to the controller, said controller comprising a predetermined set of outputs corresponding to said plurality of delivery regimens for said therapeutic agent and further comprising a receiver for receiving the signal and setting an output in response to the delivery regimen signal;
- whereby each agent can be administered according to at least one of the predetermined delivery regimens by appropriate selection of a therapeutic agent containing unit having the corresponding delivery regimen signal.

* * * * *